(12) United States Patent
Owens et al.

(10) Patent No.: US 6,455,718 B1
(45) Date of Patent: Sep. 24, 2002

(54) HALOGEN EXCHANGE REACTIONS IN PREPARING CATALYSTS AND THEIR PRECURSORS

(75) Inventors: David W. Owens; John F. Balhoff, both of Baton Rouge, LA (US)

(73) Assignee: Albemarle Corporation, Richmond, VA (US)

(*) Notice: Subject to any disclaimer, the term of this patent is extended or adjusted under 35 U.S.C. 154(b) by 0 days.

(21) Appl. No.: 09/790,263

(22) Filed: Feb. 21, 2001

Related U.S. Application Data

(60) Division of application No. 09/316,170, filed on May 21, 1999, which is a continuation-in-part of application No. PCT/US97/21629, filed on Nov. 11, 1997, now Pat. No. 6,241,917, which is a continuation-in-part of application No. 08/754,338, filed on Nov. 22, 1996, now Pat. No. 5,824,827, and a continuation-in-part of application No. 08/756,105, filed on Nov. 25, 1996, now abandoned.

(51) Int. Cl.⁷ .............................. C07F 7/26; C07F 17/02; C07F 13/00; C07F 1/02; C07F 5/02
(52) U.S. Cl. ................................. 556/7; 556/8; 556/27; 556/45; 260/665 G; 260/665 R; 568/1; 568/6
(58) Field of Search ..................... 260/665 G, 665 R; 556/7, 8, 27, 45; 568/1, 6

(56) References Cited

U.S. PATENT DOCUMENTS

| | | | |
|---|---|---|---|
| 2,025,032 A | 12/1935 | Arnold et al. | 260/168 |
| 3,064,048 A | 11/1962 | Schramm et al. | 260/559 |
| 3,064,058 A | 11/1962 | Duesel et al. | 260/646 |

(List continued on next page.)

FOREIGN PATENT DOCUMENTS

| | | |
|---|---|---|
| AU | 285453 | 8/1965 |
| CA | 2248294 | 9/1998 |
| DE | 19702282 | 7/1998 |
| EP | 0003344 | 8/1979 |
| EP | 0120575 | 10/1984 |
| EP | 0372621 | 6/1990 |
| EP | 0693466 | 1/1996 |
| EP | 0728760 | 8/1996 |
| GB | 755668 | 8/1956 |
| GB | 866810 | 5/1961 |
| GB | 970746 | 9/1964 |
| GB | 996498 | 6/1965 |
| GB | 1004375 | 9/1965 |
| GB | 1026290 | 4/1966 |
| GB | 1256082 | 12/1971 |
| GB | 1340421 | 12/1973 |
| GB | 1360327 | 7/1974 |
| GB | 1071323 | 6/1997 |
| SU | 241418 | 4/1969 |
| SU | 296748 | 3/1971 |
| SU | 341786 | 6/1972 |
| SU | 426992 | 5/1974 |
| SU | 678864 | 4/1994 |
| WO | 9200270 | 1/1992 |
| WO | 9805610 | 2/1998 |

OTHER PUBLICATIONS

Aksenov et al., "Interaction of Chloroaromatic Compounds With Alkali Metal Fluorides In The Presence of Crown–Ethers", Journal of Fluorine Chem., vol. 28, 1985, pp. 73–87.

Banks et al., "Halex Fluorination of Chlorinated Benzaldehydes And Benzoyl Chlorides", Journal of Fluorine Chem., vol. 46, 1990, pp. 529–537.

Banks et al., "Heterocyclic Polyfluoro–compounds. Part VI. Preparation of Pentafluoropyridine and Chlorofluoropyridines from Pentachloropyridine", J. Chem. Soc., 1965, pp. 594–597.

Birchall et al., "Polyfluoroarenes. Part XVI. A Convenient Synthesis of Pentafluorobenzonitrile", J. Chem. Soc., (c), 1971, pp. 1341–1342.

Böhme et al., "Synthese und Eigenschaften von Carbimidoylfluoriden", Tetrahedron Letters, No. 16, 1978, pp. 1429–1432 (Pergamon Press), (not translated).

Boudakian, Max M., "Solvent–free Fluorination of Partially–chlorinated Hetercyclics: Synthesis of 2,6–Difluoropyridine from 2,6–Dichloropyridine", J. Heterocyclic Chem., 1968, vol. 5, pp. 683–684.

(List continued on next page.)

Primary Examiner—Johann Richter
Assistant Examiner—J. Parsa
(74) Attorney, Agent, or Firm—Philip M. Pippenger

(57) ABSTRACT

Chloropentafluorobenzene or bromopentafluorobenzene is formed by heating perhalobenzene, $C_6F_nX_{6-n}$ where n is 0 to 4, and each X is, independently, a chlorine or bromine atom, with alkali metal fluoride, and an aminophosphonium catalyst (e.g., $(Et_2N)_4PBr$). The resultant chloropentafluorobenzene or bromopentafluorobenzene can be converted into a pentafluorophenyl Grignard reagent or a pentafluorophenyl alkali metal compound. This in turn can be converted into tris(pentafluorophenylborane), which can be converted into a single coordination complex comprising a labile tetra(pentafluorophenyl)boron anion (e.g., a trialkylammonium tetra(pentafluorophenyl)boron complex or an N,N-dimethylanilinium tetra(pentafluorophenyl)boron complex). The complex can be used in the preparation of an active catalyst by mixing the complex with a cyclopentadienyl metal compound containing a Group 4 metal in suitable solvent or diluent so that the cation of the complex reacts irreversibly with a ligand of the cyclopentadienyl compound, and such that the pentafluorophenyl anion forms a non-coordinating ion pair with a resulting cation produced from the cyclopentadienyl metal compound. Alternatively, the tris(pentafluorophenylborane) can be contacted with a metallocene of the formula $LMX_2$ wherein L is a derivative of a delocalized pi-bonded group imparting a constrained geometry to the metal active site and where L contains up to 50 non-hydrogen atoms, M is a Group 4 metal, and each X is, independently, hydride, or a hydrocarbyl, silyl, or germyl group having up to 20 carbon, silicon, or germanium atoms to form a catalyst having a limiting charge separated structure of the formula $LMX\oplus \; XA\ominus$ wherein A is an anion formed from the tris(pentafluorophenyl)borane.

37 Claims, 1 Drawing Sheet

U.S. PATENT DOCUMENTS

| | | | |
|---|---|---|---|
| 3,231,625 A | 1/1966 | Nyman | 260/650 |
| 3,240,824 A | 3/1966 | Boudakian et al. | 260/646 |
| 3,277,192 A | 10/1966 | Fielding | 260/650 |
| 3,280,124 A | 10/1966 | Boudakian et al. | 260/251 |
| 3,296,269 A | 1/1967 | Boudakian | 260/290 |
| 3,300,537 A | 1/1967 | Bennett et al. | 260/649 |
| 3,303,197 A | 2/1967 | Haszeldine et al. | 260/290 |
| 3,312,746 A | 4/1967 | Fielding | 260/650 |
| 3,314,955 A | 4/1967 | Boudakian et al. | 260/251 |
| 3,334,150 A | 8/1967 | Pierce et al. | 260/650 |
| 3,388,174 A | 6/1968 | Fielding et al. | 260/650 |
| 3,408,412 A | 10/1968 | Blackley et al. | 260/650 |
| 3,412,162 A | 11/1968 | Musgrave | 260/665 |
| 3,429,935 A | 2/1969 | Wall et al. | 260/650 |
| 3,453,337 A | 7/1969 | Bennett et al. | 260/650 |
| 3,485,839 A | 12/1969 | Fuller | 260/251 |
| 3,574,775 A | 4/1971 | Fuller | 260/650 |
| 3,852,365 A | 12/1974 | Mahler | 260/650 F |
| 3,965,197 A | 6/1976 | Stepniczka | 260/623 H |
| 4,069,262 A | 1/1978 | Kunz | 260/646 |
| 4,174,349 A | 11/1979 | Evans et al. | 260/544 F |
| 4,209,456 A | 6/1980 | Billenstein et al. | 260/458 F |
| 4,209,457 A | 6/1980 | Fuller | 260/465 G |
| 4,226,811 A | 10/1980 | Oeser et al. | 568/937 |
| 4,229,365 A | 10/1980 | Oeser et al. | 260/465 G |
| 4,287,374 A | 9/1981 | North | 568/937 |
| 4,543,217 A | 9/1985 | Erpenbach et al. | 260/544 A |
| 4,684,734 A | 8/1987 | Kaieda et al. | 546/345 |
| 4,937,397 A | 6/1990 | Pews et al. | 570/147 |
| 4,978,769 A | 12/1990 | Kysela et al. | 558/423 |
| 5,061,818 A | 10/1991 | Burton et al. | 558/84 |
| 5,315,043 A | 5/1994 | Fernandez et al. | 568/932 |
| 5,476,976 A | 12/1995 | Schach et al. | 638/938 |
| 5,488,169 A * | 1/1996 | Ikeda et al. | 568/3 |
| 5,545,759 A | 8/1996 | Ikeda et al. | 568/6 |
| 5,693,261 A | 12/1997 | Krzystowezyk et al. | 260/665 G |
| 5,789,631 A | 8/1998 | Balhoff et al. | 570/147 |
| 5,824,827 A | 10/1998 | Bildinov et al. | 570/147 |

OTHER PUBLICATIONS

Bunnet et al., "Aromatic Nucleophilic Substitution Reactions", Chemical Reviews, vol. 48, 1951, pp. 273–277 and 405.

Chambers et al., "Polyfluoro–heterocyclic Compounds. Part I. The Preparation of Fluoro–, Chlorofluoro–, and Chlorofluorohydro–pyridines.", J. Chem. Soc., 1964, pp. 3573–3576.

Finger et al., "Aromatic Fluorine Compounds. XI. Replacement of Chlorine by Fluorine in Halopyridines", J. Org. Chem., 1963, vol. 28, pp. 1666–1668.

Finger et al., "Aromatic Fluorine Compounds. VIII. Plant Growth Regulators and Intermediates", J. Am. Chem. Soc., 1959, vol. 81, pp. 94–101.

Finger et al., "Aromatic Fluorine Compounds. VII. Replacement of Aromatic–C1 and –NO$_2$ Groups by –F$^{1,2}$" J. Am. Chem. Soc., 1956, vol. 78, pp. 6034–6037.

Fuller et al., "Preparation of Polyfluoroaromatic Compounds by the Reaction of Perhalogeno–aromatic Compounds with Potassium Fluoride in Sulpholan" J. Chem. Soc., 1965, pp. 6264–6267.

Furin et al., "Fluoroaromatic Compounds", Syntheses of Fluoroorganic Compounds, 1985, edited by I.L. Knunyants and G. G. Yakobson, Springer–Verlag, pp. 109–232.

Gottlieb, Hans Billroth, "The Replacement of Chlorine by Fluorine in Organic Compounds", J. Am. Chem. Soc., 1936, vol. 58, pp. 532–533.

Harper, Jr. et al., "Reactions of Organometallics with Fluoroaromatic Compounds", Journal of Organic Chemistry, 1964, vol. 29, pp. 2385–2389.

Heller, Adam, "Preparation of 3–Fluorophthalic Anhydride", J. Org. Chem., 1960, vol. 25, pp. 834–835.

Hitze, J., "La Fluoration Par Kf De Perhalogenes Organiques Aromatiques En Presence De Faibles Quantites De Sulfolane Ou D'eau. Spectres De Masses Des Melanges Obtenus En Serie Benzenique", J. Fluorine Chem. vol. 18, 1981, pp. 101–115 (not translated).

Hitzke et al., "No. 163. Preparation de derives perhalogenes aromatiques polyfluores par reaction d'echange d'halogene, utilisant une phase sel fondu", Bulletin de al Societe Chimique de France, 1974, No. 5–6, pp. 811–814 (not translated).

Hitzke, J., "La Fluoration De L'Hexachlorobenzene et de la Pentachloropyridine en Milieu de Fluorure de Potassium Solide", J. Fluorine Chem., vol. 16, 1980, pp. 103–128 (not translated).

Holbrook et al., "Fluorination of Perhalobenzenes with Potassium Fluoride in Polar Solvents", J. Org. Chem., 1966, vol. 31, pp. 1259–1261.

Kimura et al., "Halex Fluorination of 1,2,4,5–Tetrachlorobenzene in a Pressure Reactor", J. Of Fluorine Chemistry, vol. 59, 1992, pp. 289–291.

Koidan et al., "Some Properties of Phosphorimidic Triamides", Zhurnal Obshchei Khimi, vol. 52, No. 9, 1982, pp. 2001–2011, (English translation pp. 1779–1787).

Kobayashi, Etsuro, "Studies on Nitrogen–Phosphorus Compounds. XXII. The Synthesis and Properties of Phosphoric Aniline Diamide", Bulletin of the Chemical Society of Japan, vol. 46, No. 1, 1973, pp. 183–186.

Kovenya et al., "Properties of Pentaalkylphosphorodiamidimidic Chlorides" Translated from Zhurnal Obshchei Khimii, vol. 51, No. 12, 1981, pp. 2678–2684, (translated pp. 2310–2314).

Confidential Unpublished Report dated Mar. 1996 to Albemarle Corporation from another party, 139 pages.

Lambert et al., "The Trimesitylsilylium Cation", Angew. Chem. Int. Ed. Engl., 1997, vol. 36, No. 4, pp. 400–401.

Liotta et al., "The Chemistry of "Naked" Anions. I. Reactions of the 18–Crown–6 Complex of Potassium Fluoride with Organic Substrates in Aprotic Organic Solvents", J. Am. Chem. Soc., 1974, vol. 96, No. 7, pp. 2250–2252.

Lundin et al., "Investigation of Methods of Preparing Polyfluoromatic Compounds", Trudy Instituta Khimii, vol. 16, 1968, pp. 67–73. (Also 15 pages translated).

Marchenko et al., "Reactions of Tetrakis (Dialkylamino) Phosphonium Bromides with Bases", 1984, Translated from Zhurnal Obshchei Khimii, vol. 54, No. 12, pp. 2691–2696.

Marchenko et al., "Chlorotris(Dialkylamino)Phosphonium Chlorides", Translated from Zhurnal Obshchei Khimii, vol. 48, No. 3, 1978, pp. 551–558.

Marchenko et al., "N–Chlorophosphorimidic Triamides", Translated from Zhurnal Obshchei Khimii, 1983, vol. 53, No. 3, pp. 670–677.

Marchenko et al., CAPLUS Abstract, "Ammonolysis of Triamidohalophosphonium Halides", 1980.

Maynard, John T., "The Synthesis of Highly Fluorinated Compounds by Use of Potassium Fluoride in Polar Solvents", J. Org. Chem., 1963, vol. 28, pp. 112–115.

Nield et al., "Aromatic Polyfluoro–compounds. Part I. The Synthesis of Aromatic Polyfluoro–compounds from Pentafluorobenzene", Journal of The Chem. Soc., 1959, pp. 166–171.

Pearson et al., "The Synthesis of Pentafluorobenzoic Acid and a New Purification of Chloropentafluorobenzene", Communications, Georg Thieme Publishers, 1978, pp. 127.

Smyth et al., "Inexpensive, Active KF for Nucleophilic Aromatic Displacement Reactions", Tetrahedron, 1995, vol. 51, No. 22, pp. 6363–6376.

Starr et al., "Dimethyl Sulphone as a Reaction Solvent for the Preparation of Aromatic Fluorides", Chemistry and Industry, 1962, pp. 1328–1329.

Stuebe et al., "Preparation of Some Hexaalkyl–phosphorous, Phosphoric and Phosphorothioic Triamides", J. Am. Chem. Soc., 1956, vol. 78, pp. 976–977.

Suzuki et al., "Tetraphenylphosphonium Bromide–catalyzed 'Halex' Fluorination of Chloroaryl Sulfonyl Chlorides", Journal of Fluorine Chemistry, 1991, vol. 55, pp. 335–337.

Tamborski et al., "Perfluoro Tertiary Alcohols", Journal of Organic Chemistry, 1966, vol. 31, pp. 4229–4230.

Vargha et al., "Synthesis of New Sugar Derivatives of Potential Antitumour Activity. Part. I Ethyleneimino– and 2–Chloroethylamino–derivatives", J. Chem. Soc., 1957, pp. 805–809.

Vorozhtsov, Jr. et al., "Aromatic fluoroderivatives. VIII. Reaction of Chloronitro Compounds with Fluorides of Alkali Metals", Chem. Abstracts, vol. 57, 1962, Col. 9706–9707.

Vorozhtsov et al., "Preparation of Hexafluorobenzene From Hexachlorobenzene", Izv. Akad. Nauk, SSSR Ser. Khim. No. 8, 1963, pp. 1524,(Translated).

Vorozhtsov et al., "Formation of Chloroheptafluorotoluenes in the Reaction of Hexachlorobenzene with Potassium Fluoride", Zhurmal Vsesoyuznoe Khimicheskoe Obschestvo im. D.I. Medeleeve, vol. 14, No. 1, 1969, pp. 114. (Also 3 Translated pages).

Yakobson et al., "Aromatic Fluorine Derivatives XVI. Preparation of Hexafluorobenzene and Polyfluorochlorobenzenes", Ahur. Obs. Khimii, vol. 35, No. 7, 1965, pp. 1158–1161. (Translated pp. 1161–1164).

CAPLUS Abstract of JP Patent 49110637, 1975.

Chemical Abstract SU Patent 426992,1974.

Chemical Abstract SU Patent 341786, 1972.

Chemical Abstract SU Patent 296748, 1971.

Chemical Abstract SU Patent 241418, 1969.

Chemical Abstract, SU Patent 199901, 1967.

Pushkina et al., Chemical Abstract, Journal Ref., "Methods of Preparation and Properties of Organofluorine Compounds", Zh. Obshch. Khim. 1966.

Sokolov et al., Chemical Abstract, Journal Ref., "Methods of Preparation and Properties of Organofluorine Compounds. V. The Magnitude of Chemical Shifts in N.M.R. Spectra of Perfluorinated Nitrogenous Heterocyclic Compounds", Zh. Obshch. Khim., 1966.

Mazalova et al., Chemical Abstract, Journal Ref., "Reaction of Some Derivatives of .omega., .omega., .omega.–trichlorohexafluorovaleric Acid With Copper", Zh. Obshch. Khim., 1966.

* cited by examiner

HALOGEN EXCHANGE REACTIONS IN PREPARING CATALYSTS AND THEIR PRECURSORS

REFERENCE TO RELATED APPLICATIONS

This is a divisional of U.S. application Ser. No.09/316,170, filed May 21, 1999 now issued as U.S. Pat. No. 6,241,917 which in turn is a continuation-in-part of International Application PCT/US97/21629, with an international filing date of Nov. 11, 1997, which in turn is a continuation in Part and claims priority on prior U.S. application Ser. Nos. 08/754,338, filed Nov. 22, 1996, now U.S. Pat. No. 5,824,827, and 08/756,105, filed Nov. 25, 1996, now abandoned. Said International Application has been published in English.

TECHNICAL FIELD

This invention relates to halogen exchange reactions involving haloaromatic compounds and alkali metal fluorides, and more particularly to improved processes for producing polyfluorinated aromatics by catalyzed halogen exchange reactions, and to industrially important applications of such process technology.

BACKGROUND

Halogen exchange reactions for fluorinating haloaromatic compounds using alkali metal fluorides have been extensively studied heretofore. Typically they involve the reaction of a chloroaromatic compound with potassium fluoride, rubidium fluoride or cesium fluoride by heating the reactants to extremely high temperatures (above about 400° C.) in the absence of an ancillary diluent or solvent, or by conducting the reaction at temperatures of around 200° to 230° C. in an aprotic solvent such as sulfolane. It has also been reported that organic fluorine compounds such as pentafluorobenzonitrile, tetrafluoro-phthalonitriles and pentafluoropyridine can be formed by reacting a corresponding chloro- or bromo-substituted compound with alkali metal halide such as potassium fluoride in benzonitrile as solvent at 190° C. to 400° C. in a sealed autoclave under autogenous pressure.

Use of catalysts in some exchange reactions has also been studied. Such catalysts have included quaternary ammonium salts, metal carbonyls, crown ethers and cryptates.

In most cases, the halogen exchange reaction is sluggish and tends to form product mixtures in which yields of polyfluorinated aromatics are relatively low, especially if the haloaromatic compound used is a polyhaloaromatic compound free from activating functionality such as nitro or carbonyl. For example, with hexachlorobenzene and potassium fluoride, typical product mixtures contain a mixture of co-products including hexafluorobenzene together with various chlorofluorobenzenes.

A need presently exists for a commercially feasible process whereby the halogen exchange reaction as applied to a wide variety of haloaromatic compounds may be conducted in large scale reaction equipment under relatively mild reaction conditions while providing commercially acceptable yields of the desired products. In addition, a particularly welcome contribution to the art would be the provision of a process whereby fluorinated perhaloaromatic compounds such as chloropentafluorobenzene, bromopentafluorobenzene, and hexafluorobenzene can be produced on a large scale in good yield under relatively mild reaction conditions, thereby making possible the more efficient, lower cost production of a variety of industrially important end products, especially polymerization catalysts, and intermediates for producing such catalysts.

This invention is deemed to fulfill these needs most expeditiously.

SUMMARY OF THE INVENTION

This invention provides a new catalytic halogen exchange reaction using an alkali metal fluoride as the fluorine source. The process enables production of a wide variety of fluorinated aromatic compounds under relatively mild reaction conditions. Moreover, the process is applicable to use as starting materials of haloaromatic compounds containing one or more halogen atoms other than fluorine, including compounds which are devoid of activating groups, as well as compounds which possess one or more activating groups in the molecule. In fact, the process is especially well adapted for polyfluorination of perhaloaromatic compounds such as hexachlorobenzene, hexabromobenzene, pentachlorofluorobenzene, tetrachlorodifluorobenzene, trichlorotrifluorobenzene, dichlorotetrafluorobenzene, etc., which have no activating group in the molecule. In addition, the catalyzed process can be conducted with smaller excesses of the alkali metal fluoride than generally required in prior processes.

More particularly, there is provided pursuant to one of the embodiments of this invention a process which comprises (A) heating a mixture formed from ingredients comprising (i) at least one finely-divided alkali metal fluoride having an atomic number of 19 or more, (ii) at least one perhalobenzene of the formula $C_6F_nX_{6-n}$ where n is 0 to 4, and each X is, independently, a chlorine or bromine atom, and (iii) an aminophosphonium catalyst, at one or more reaction temperatures at which chloropentafluorobenzene or bromopentafluorobenzene is formed; (B) recovering chloropentafluorobenzene or bromopentafluorobenzene formed in (A); and (C) converting chloropentafluorobenzene or bromopentafluorobenzene from (B) into a pentafluorophenyl Grignard reagent or a pentafluorophenyl alkali metal compound.

In another embodiment, the above process further comprises (D) converting pentafluorophenyl Grignard reagent or pentafluorophenyl alkali metal compound from (C) into a pentafluorophenyl boron compound by reacting the pentafluorophenyl Grignard reagent or pentafluorophenyl alkali metal compound with a boron trihalide or an etherate complex thereof.

Yet another embodiment of this invention further comprises (E) converting pentafluorophenyl boron compound from (D) in a suitable solvent or diluent into a single coordination complex comprising a labile tetra (pentafluorophenyl)boron anion.

Still another embodiment of this invention further comprises (E) contacting such pentafluorophenyl boron compound from (D) with a metallocene of the formula $LMX_2$ wherein L is a derivative of a delocalized pi-bonded group imparting a constrained geometry to the metal active site and contains up to 50 non-hydrogen atoms, M is a Group 4 metal, and each X is, independently, hydride, or a hydrocarbyl, silyl, or germyl group having up to 20 carbon, silicon, or germanium atoms under conditions to form a catalyst having a limiting charge separated structure of the formula $LMX \oplus XA \ominus$ wherein A is an anion formed from said pentafluorophenyl boron compound.

The substantial improvements made possible by this invention are brought about at least in part by use of an aminophosphonium catalyst in the halogen exchange reaction. As an example of such improvements, comparative studies on a 50-liter scale have shown that in reactions using hexachlorobenzene and potassium fluoride to form chloropentafluorobenzene and hexafluorobenzene, the inclusion of the aminophosphonium catalyst, tetrakis(diethylamino) phosphonium bromide, in the reaction mixture resulted in the following yield improvements:

a) Yields of desired products based on raw material inputs were increased from 12% to 25%.

b) Yields of desired products based on hexachlorobenzene input were increased from 35% to 95%.

c) Molar yields of desired products were increased from 49% to 86%.

In conducting the halogen exchange process, an agitated mixture formed from ingredients comprising (i) at least one finely-divided alkali metal fluoride, (ii) at least one haloaromatic compound having on an aromatic ring at least one halogen atom of atomic number greater than 9, such haloaromatic compound being devoid of any activating functional group on the aromatic ring to which the halogen atom of atomic number greater than 9 is bonded, and (iii) an aminophosphonium catalyst, is heated at one or more reaction temperatures at which at least one such halogen atom of the haloaromatic compound is replaced by a fluorine atom. It is particularly preferred to use as the initial haloaromatic ingredient to be subjected to the halogen exchange processing, one or more haloaromatic compounds that are not only devoid of any activating functional group on the aromatic ring to which the halogen atom of atomic number greater than 9 is bonded, but in addition have no hydrogen atom on that aromatic ring.

Another preferred embodiment includes conducting the halogen exchange reaction such that the essentially anhydrous agitated mixture when heated to one or more reaction temperatures is predominately a mixture of solids dispersed in a continuous liquid phase. Operations wherein the continuous liquid phase comprises at least one halogen-free, polar, anhydrous aprotic solvent constitute additional preferred embodiments of this invention.

Preferred catalyst ingredients for use in the various process embodiments of this invention are tetra (dihydrocarbylamino)phosphonium halides.

These and other embodiments, features and advantages of this invention will be further apparent from the ensuing description, accompanying drawing, and appended claims.

FURTHER DESCRIPTION OF THE INVENTION

I. THE HALOGEN EXCHANGE PROCESS

Figure 1:
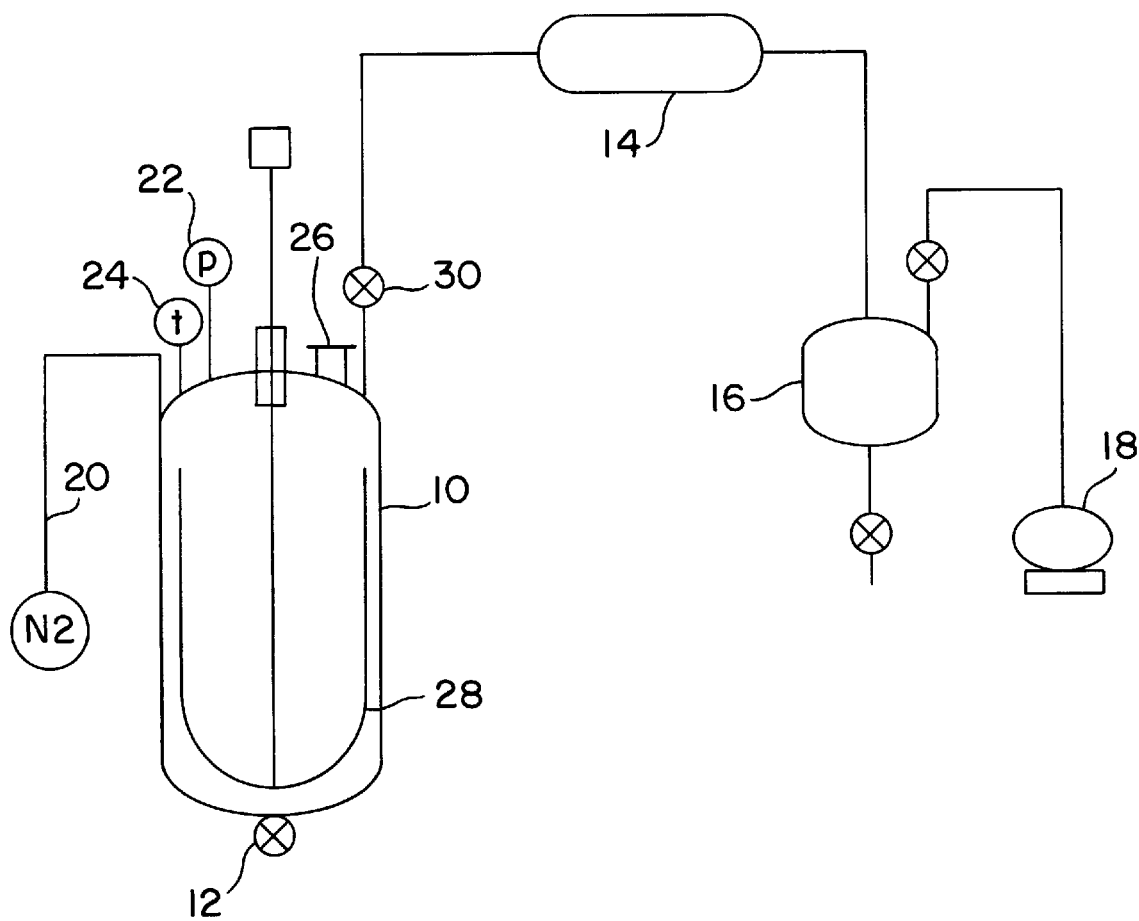
FIG. 1 illustrates schematically a batch type plant facility for conducting the halogen exchange process without use of an ancillary solvent/diluent.

The halogen exchange reaction described herein is applicable to a wide variety of haloaromatic compounds containing one or more ar-halogen atoms other than fluorine, and this is reflected in this Section I of the disclosure.

The basic feed materials to the process are one or more haloaromatic compounds containing one or more ar-halogen atoms other than fluorine, alkali metal fluoride(s) of one or more alkali metals other than lithium (preferably alkali metal of atomic number 19 or above), and one or more aminophosphonium catalysts. Use of one or more ancillary solvents or diluents is optional, but preferable.

Haloaromatic Ingredient

Any aromatic compound that has at least one replaceable halogen atom other than fluorine on the aromatic ring is a candidate ingredient for use in the process. The compound may have a homocyclic aromatic nucleus (i.e., at least one benzene ring system) or a heteroaromatic ring system. Also, the compound may contain one or more activating groups such as nitro, nitroso, carbonyl, cyano, sulfonic acid, etc., or it may be devoid of any such group. The compound contains one or more chlorine, bromine or iodine atoms, or any combination of Cl, Br, and/or I atoms on the aromatic ring and may also have one or more such halogen atoms on one or more side chains and/or on one or more non-aromatic homocyclic or heterocyclic rings bonded or fused to the aromatic ring system. In addition the compound may contain one or more fluorine atoms anywhere in the molecule including one or more ar-fluorine atoms provided the compound has at least one aromatic ring that contains at least one replaceable ar-halogen atom other than fluorine. The hetero atom in the halo-substituted aromatic ring where the fluorine substitution is desired is from 1 to 3 nitrogen atoms (e.g., the compound is, or has at least the ring system of, an ar-halopyridine, an ar-halopyridazine, an ar-halopyrimidine, an ar-halopyrazine, an ar-halotriazine where at least one ar-halogen atom is other than a fluorine atom). Other hetero atoms which can be present in side chains or additional ring systems of the compound include one or more nitrogen, oxygen, sulfur, phosphorus, boron or silicon atoms, or combinations of two or more of these. Generally speaking, the haloaromatic ingredient may contain in the range of up to 50 carbon atoms in the molecule, and preferably contains in the range of up to 20 carbon atoms in the molecule.

Preferred are haloaromatic compounds that are devoid of any activating group(s) in the molecule, as these usually undergo a halogen exchange reaction much less readily than their counterparts which have activating functionality in the molecule.

As between the homocyclic and heterocyclic haloaromatics, the homocyclic haloaromatics are preferred ingredients. As noted above, haloaromatics that are devoid of any activating functional group on the aromatic ring to which the halogen atom of atomic number greater than 9 is bonded and in addition, are devoid of any hydrogen atom on that aromatic ring constitute another preferred category of haloaromatic ingredient or feed material for the process. Moreover, there is a particularly pressing present need for methods for effectively producing polyfluorobenzenes, especially chloropentafluorobenzene and hexafluorobenzene, from their polychloro analogs such as hexachlorobenzene, pentachlorofluorobenzene, tetrachlorodifluorobenzene, trichlorotrifluorobenzene, or dichlorotetrafluorobenzene, or mixtures of any two or more of these, to thereby make possible the more efficient, lower cost production of a variety of industrially important end products, especially polymerization catalysts, and intermediates for producing such catalysts, a need fulfilled by this invention.

Also fulfilled by this invention is the need for a method for effectively producing bromopentafluorobenzene from its polybromo analogs such as hexabromobenzene, pentabromofluorobenzene, tetrabromodifluorobenzene, tribromotrifluorobenzene, or dibromotetrafluorobenzene, or mixtures of any two or more of these.

Other haloaromatic compounds which can be converted into ar-fluorinated compounds by use of this halogen exchange process include, for example, mono-, di-, tri-, tetra- and pentachlorobenzenes, and bromo and iodo analogs thereof; mono and polychloro, bromo and iodo naphthalenes, tetrahydronaphthalenes, acenaphthalenes, biphenyls and terphenyls; alkyl- and haloalkyl-substituted analogs of the foregoing; chloro, bromo and iodo diarylethers and monoalkylmonoaryl ethers; 2-chloronitrobenzene; 4-chloronitrobenzene; 2,4-dinitrochlorobenzene; 3,4-dichloronitrobenzene; 3-chloro-4-fluoronitrobenzene; 2,4,6-trichloropyrimidine; tetrachloropyrimidine; 2-chlorobenzonitrile; 4-chlorobenzonitrile; pentachlorobenzonitrile; tetrachloroisophthalonitrile; 2-chloropyridine; 2,5-dichloropyridine; pentachloropyridine; 4-chlorophthalic anhydride; and still other similar compounds, such as are referred to in U.S. Pat. No. 4,684,734 to Kaieda, et al.

Alkali Metal Fluoride Ingredient

Potassium fluoride, rubidium fluoride, and cesium fluoride are the preferred alkali metal halides used in the practice of the halogen exchange process because of their higher reactivity in the exchange reaction. However, sodium fluoride can be used, especially where the haloaromatic ingredient has activating functionality on the haloaromatic ring, and in cases where only partial replacement of ar-chloride, ar-bromide or ar-iodide is desired.

Combinations of any two or more of the alkali metal fluorides can be used, including combinations in which lithium fluoride is present. Thus, mixtures of potassium fluoride, rubidium fluoride and/or cesium fluoride together with sodium fluoride or lithium fluoride, or both, can also be used if desired, although this is not recommended. To enhance its reactivity, the alkali metal fluoride should be in finely-divided or powdery anhydrous form. Potassium fluoride is the preferred fluorinating agent as it is the most cost effective reagent. One convenient way of ensuring that the fluorinating agent is suitably anhydrous is to form a slurry of the fluoride salt in a suitable volatile hydrocarbon such as benzene that forms an azeotrope with water, and heat the mixture to dryness, while of course suitably handling and disposing of the vapors. A particularly useful form of potassium fluoride for use in the process is the active form of KF produced using the procedure described by T. P. Smyth, A. Carey and B. K. Hodnett in *Tetrahedron*, Volume 51, No. 22, pp.6363–6376 (1995). In brief, the procedure involves recrystallizing KF from a methanol solution by slow evaporation of the solvent, followed by drying at 100° C. Another useful form of potassium fluoride is KF dispersed on $CaF_2$. This material is described by J. H. Clark, A. J. Hyde and D. K. Smith in *J Chem. Soc. Chem. Commun*, 1986, 791. Other activated forms of KF such as spray dried KF (N. Ishikawa, et al. *Chem. Letts*, 1981, 761), and freeze dried KF (Y. Kimura, et al. Tetrahedron Letters, 1989, 1271) can be used. It is also deemed possible to apply one or more of the foregoing activating procedures to other alkali metal fluorides such as cesium fluoride and/or sodium fluoride. The entire disclosure of each of the four papers cited in this paragraph is incorporated herein by reference.

To enhance its reactivity, the alkali metal fluoride as charged to the reaction mixture is preferably in finely-divided or powdery anhydrous or substantially anhydrous form, i.e., it should not contain, if any, more than about 3000 parts per million (ppm) of water on a weight basis. Potassium fluoride is the preferred fluorinating agent as it is the most cost-effective reagent, and most preferably it will have a water content, if any, below about 1000 ppm. Ordinarily the alkali metal fluoride particles should have an average surface area of at least about 0.20 $m^2/g$. In this connection, the larger the average surface area of the alkali metal fluoride particles, the better. Thus it is preferred that the alkali metal fluoride initially have an average surface area of at least about 0.40 $m^2/g$, and more preferably at least about 0.80 $m^2/g$. For example, as charged to the reactor, spray dried potassium fluoride with a typical water content of about 1000 ppm and an average surface area of about 0.85 $m^2/g$ has been found to give a reaction rate that is approximately four times the rate given under the same conditions by spray dried potassium fluoride with an average surface area of about 0.25 $m^2/g$.

The proportions of alkali metal fluoride to the haloaromatic ingredient(s) being used can be varied. In theory there is no upper limit on the amount of alkali metal fluoride used relative to the amount of haloaromatic compound(s) used. If a very large excess of alkali metal fluoride is used relative to the amount of replaceable halogen present in the haloaromatic ingredient(s) present, the latter becomes the limiting reactant and the excess alkali metal halide remains as such. When the reaction is performed in the absence of an ancillary diluent, an excess amount of the alkali metal fluoride can serve to facilitate stirring or other agitation of the reaction mixture, and thus to this extent use of a suitable excess of alkali metal fluoride can be beneficial. Nevertheless, beyond a certain level of excess alkali metal fluoride, common sense and practicality come into play. Thus ordinarily the amount of alkali metal fluoride will not exceed about 10 or 15 moles per mole of replaceable halogen in the initial haloaromatic ingredient(s) used, and in most cases will be less than this. If on the other hand the amount of replaceable halogen in the haloaromatic ingredient(s) used exceeds the molar quantity of alkali metal fluoride used, the latter becomes the limiting reactant. Thus in most cases this factor will also be taken into consideration when selecting the proportions for use in any given reaction. Generally speaking, the reactants will often be employed in proportions falling in the range of from about 0.8 to about 5 moles of alkali metal fluoride per mole of replaceable halogen in the haloaromatic ingredient(s) used therewith, and in some preferred cases such as where an ancillary diluent is employed, the reactants will be charged in proportions in the range of from about 1 to about 3 moles of alkali metal fluoride per mole of replaceable halogen in the haloaromatic ingredient(s) used therewith.

Aminophosphonium Catalyst Ingredient

An essential catalyst ingredient of the present halogen exchange process is at least one aminophosphonium catalyst ingredient. One or more other co-catalysts may also be included, if desired, as long as at least one aminophosphonium catalyst ingredient is charged, concurrently or in any sequence, into the reaction zone or reaction mixture. Use of the aminophosphonium catalyst without use of a co-catalyst is currently deemed preferable.

The aminophosphonium catalysts are preferably charged in the form of tetra(dihydrocarbylamino)phosphonium halides. Such compounds can be represented by the formula:

$$(R_2N)_4P \oplus X \ominus$$

where each R is, independently, a hydrocarbyl group, preferably an alkyl group, and X is a halogen atom, preferably a fluorine or bromine atoms, and most preferably a bromine atom. Examples of such aminophosphonium compounds are:

tetrakis(diethylamino)phosphonium fluoride
tetrakis(dibutylamino)phosphonium bromide
tris(diethylamino)(dipropylamino)phosphonium iodide
tetrakis(dibutylamino)phosphonium iodide
tris(dibutylamino)(diethylamino)phosphonium iodide
tris(dipropylamino)(diheptylamino)phosphonium iodide tetrakis(dipropylamino)phosphonium bromide
tris(diethylamino)(dihexylamino)phosphonium iodide
tris(diethylamino)(dibutylamino)phosphonium iodide
tris(dipropylamino)(heptylpropylamino)phosphonium iodide
tetrakis(dipropylamino)phosphonium iodide
tris(dipropylamino)(ethylpropylamino)phosphonium iodide
tetrakis(diethylamino)phosphonium iodide
tetrakis(diethylamino)phosphonium bromide
tetrakis(diphenylamino)phosphonium bromide
tetrakis(di-m-tolylamino)phosphonium bromide
tetrakis(dibenzylamino)phosphonium bromide
tetrakis(dicyclohexylamino)phosphonium bromide
tetrakis(dioctylamino)phosphonium bromide
tetrakis(didecylamino)phosphonium bromide
tetrakis(diethylamino)phosphonium chloride
tetrakis(dipropylamino)phosphonium chloride
tetrakis(dibutylamino)phosphonium chloride
tetrakis(dihexylamino)phosphonium chloride.

One preferred group of aminophosphonium catalyst in the form as charged to the reactor is comprised of the tetra(dialkylamino)phosphonium chlorides and/or bromides. Of these, the aminophosphonium catalyst ingredient is more preferably one or more tetra(dialkylamino)phosphonium bromides in which the alkyl groups can be the same or different and each has up to about 12 carbon atoms. At present, the most preferred compound is tetrakis(diethylaminophosphonium bromide. For a method for the preparation of such compounds, see Koidan, Marchenko, Kudryavtsev, and Pinchuk, $Zh.\ Obshch.\ Khim.$, 1982, 52, 2001, an English language translation of which is available from Plenum Publishing Corporation.

A procedure which has been used for preparing tetra(diethylamino)phosphonium bromide involves the following four steps (where Et represents an ethyl group):

1) $PCl_3 + 6HN(Et)_2 + CCl_4 \rightleftharpoons (Et_2N)_3P\oplus -CCl_3Cl\ominus \rightleftharpoons (Et_2N)_3P=CCl_2$
2) $(Et_2N)_3P\oplus -CCl_3Cl\ominus + NH_3 \rightarrow (Et_2N)_3P=NH\cdot HCl + CHCl_3$
3) $(Et_2N)_3P=NH\cdot HCl + NaOH \rightarrow (Et_2N)_3P=NH + NaCl + H_2O$
4) $(Et_2N)_3P=NH + 2NaOH + 2EtBr \rightarrow [(Et_2N)]_4PBr + 2NaBr + 2H_2O$ In this procedure, carbon tetrachloride and phosphorus trichloride are charged to the reactor followed by the slow addition of diethyl amine at low temperature (30° C. maximum). This results in the formation of dichloromethylene phosphoroamidite intermediate. Ammonia (gas) is then charged to the reactor resulting in the formation of an imino hydrochloride phosphoroamidite intermediate. Following a period of stirring, the reactor contents are filtered, and the filtrate is concentrated by evaporation under vacuum. The concentrated filtrate is then treated with sodium hydroxide solution causing the formation of the free base imino phosphoroamidite. This is extracted with dichloromethane. The extracted solution is dried with calcium chloride and the dichloromethane is removed by evaporation. The solid product is mixed with sodium hydroxide and bromoethane is charged. This results in the formation of the product tetra(diethylamino)phosphonium bromide. The product is then extracted with dichloromethane. The extract is dried and the dichloromethane is removed by evaporation. The crude product is then recrystallized from a mixture of dichloromethane and diethyl ether. The recrystallized, wet, product is then dried.

Typical raw materials input for such sequential operations is as follows: carbon tetrachloride, 3985 grams (25.7 moles); phosphorous trichloride, 270 grams (1.96 moles); diethyl amine, 880 grams (12.39 moles); ammonia, 40 grams (2.35 moles); 50% sodium hydroxide, 315 grams; dichloromethane, 472 grams; calcium chloride (anhydrous), 23.6 grams; 20% sodium hydroxide, 534 grams; bromoethane, 230 grams (2.12 moles); dichloromethane, 1643 grams; calcium chloride (anhydrous) 82.1 grams; dichloromethane 450 grams; diethyl ether, and 450 grams. Typically this provides a yield of about 300 grams (0.754 moles) per batch.

The aminophosphonium catalyst is used in catalytically effective amounts, and such amounts typically fall in the range of about 3 to about 6 mole %, and preferably in the range of about 4 to about 5 mole %, based on the total amount (in moles) of the haloaromatic compound(s) with which the aminophosphonium catalyst is being associated in the reaction zone.

Co-catalyst Ingredient

The tetra(dihydrocarbylamino)phosphonium halide catalysts are effective when utilized as the only catalyst component charged directly or indirectly (i.e., after admixture with one or more other components being charged to the reaction system). Such catalytic mode of operation is preferred. However, as noted above, one or more co-catalyst ingredients may be used, if desired.

One type of such co-catalyst materials is comprised of one or more crown ethers or crypt compounds. These compounds, sometimes referred to as "cage compounds" can prove helpful in further enhancing the reactivity of the alkali metal fluoride. See in this connection, U.S. Pat. No. 4,174,349 to Evans, et al. A full description of the crown ethers and the crypt compounds is provided in the Evans, et al. patent and references cited therein relating to these materials, namely U.S. Pat. No. 3,687,978; J. J. Christensen, et al., $Chem.\ Rev.$, 1974, 74, 351; J. S. Bradshaw, et al., $Heterocycl.\ Chem.$, 1974, 11, 649; C. J. Pedersen, et al., $Angew.\ Chem.\ Int.\ Ed.\ Engl.$, 1972, 11, 16; the Technical Bulletin of PCR Incorporated entitled KRYPTOFIX; and $J.\ Org.\ Chem.$, 1977, Vol 42, No. 10, 2A. The crown ether or crypt compound is used in a catalytically effective amount, which typically is in the range of 0.01 to 1 mol per mol of haloaromatic compound(s) in the reaction mixture.

Another type of co-catalyst that can be used is composed of (i) at least one polyvalent inorganic fluoride of boron, aluminum, tin, phosphorus, titanium, zirconium, hafnium, or silicon, or (ii) at least one double salt of the polyvalent inorganic fluoride and alkali metal fluoride, or (iii) a combination of (i) and (ii), with the proviso that the inorganic fluoride of (i), (ii) and (iii) is in a stable valency state so that (i), (ii) and (iii), as the case may be, has no oxidizing properties. U.S. Pat. No. 3,453,337 to Bennett, et al., reports that in the uncatalyzed reaction between hexachlorobenzene and KF or NaF, the inclusion of compounds of the types (i), (ii) and (iii) above provides enhanced product yields using milder reaction conditions and shorter reaction times. Examples of suitable polyvalent compounds include $LiBF_4$, $NaBF_4$, $KBF_4$, $K_2SnF_6$, $KPF_6$, $K_2SiF_6$, $Na_2TiF_6$, $K_2TiF_6$, $Na_2ZrF_6$, $K_2ZrF_6$, $Na_2HfF_6$, $K_2HfF_6$, among others. Such compounds can be used in catalytically effective amounts of up to 50% or more of the weight of the alkali metal fluoride charged to the reaction mixture. Typically the amount will fall in the range of about 2 to about 25% of the weight of alkali metal fluoride used.

Other co-catalysts which may be considered for use include quaternary ammonium salts such as described for example by J. Dockx, *Synthesis*, 1973, 441; C. M. Starks and C. Liotta, *Phase Transfer Catalysts*, 1978, Academic Press, New York; and W. P. Weber and G. W. Gokel, *Phase Transfer Catalysis in Organic Synthesis*, 1977, Springer-Verlag, Berlin-Heidelberg-New York); and metal carbonyls such as described by M. F. Semmelhack and H. T. Hall, *J Am. Chem. Soc.*, 1974, 96, 7091.

The aminophosphonium catalyst and the above co-catalyst(s), if used, can vary both in function and in composition. As to function, they can serve to promote or enhance the fluorination exchange reaction, e.g., (a) by increasing reaction rate without affecting yield or selectivity, (b) by increasing yield or selectivity, or both, without affecting reaction rate, or (c) by increasing reaction rate and improving yield or selectivity, or both. Thus the term "catalyst" or "co-catalyst" is used herein to denote that the material in the manner used improves or enhances the reaction process in some way or other so that the inclusion or presence of that material or its progeny in the reaction mixture provides at least one beneficial consequence of its use. The mechanism by which it exerts its effect(s) is of no consequence, provided of course that the advantage(s) of its use outweigh(s) the disadvantage(s), if any, of its use.

As regards catalyst and co-catalyst composition, the material is identified herein as to its composition prior to being combined with any other substance being used in the process. After addition to, and/or mixing with, one or more other ingredients used in the process and/or during the course of the process itself, the catalyst may change in its composition, and if so, the resultant changed material, whatever its makeup and however many changes it may undergo, may be responsible in whole or in part for the functioning of the catalyst.

Process Conditions

The process can be conducted by dry mixing the finely-divided essentially anhydrous alkali metal fluoride, the haloaromatic compound having at least one halogen atom of atomic number greater than 9 on an aromatic ring, and an aminophosphonium catalyst, and heating the mixture at one or more reaction temperatures at which at least one such halogen atom of the haloaromatic compound is replaced by a fluorine atom. Alternatively, the foregoing ingredients may be heated to one or more such reaction temperatures while in admixture with an ancillary solvent/diluent. The solvent or diluent used is preferably a polar aprotic solvent such as, for example, sulfolane (tetramethylene sulfone), N,N-dimethylformamide, N,N-dimethylacetamide, dimethylsulfone, dimethylsulfoxide, triglyme (triethylene glycol dimethyl ether), N-methyl pyrrolidinone, or benzonitrile, or mixtures of two or more of such materials, and like polar aprotic solvents that are in the liquid state at the reaction temperature selected for use, and more preferably that are also in the liquid state at 10° C. or below. Benzonitrile and ring-substituted liquid alkylbenzonitriles (e.g., o-methylbenzonitrile, m-methylbenzonitrile, etc.), and especially benzonitrile itself, are the preferred solvents. Another preferred aprotic solvent is nitrobenzene because of its excellent solvency characteristics and relatively low cost. Other solvent/diluents for use in the process are haloaromatics that are in the liquid state at least at, and preferably below, the reaction temperature(s) being employed. Examples include hexafluorobenzene, octafluorotoluene, perfluorodecalin, dichlorotetrafluorobenzene, trichlorotrifluorobenzene and tetrachlorodifluorobenzene. The last three such compounds are especially desirable as solvent/diluents when producing pentachlorofluorobenzene as they not only serve as solvent/diluents, but as reactants as well.

Whether the reaction mixture is formed with or without a solvent/diluent, the reaction mixture should be thoroughly agitated during the course of the reaction to ensure intimate contact among the different materials in the mixture. Thus use of mechanical agitation equipment such as mechanical stirrers, rocking autoclaves, or similar apparatus is highly recommended.

Reaction temperatures will typically be in the range of about 150° C. to about 350° C. and preferably in the range of about 170° C. to about 250° C. When the process is conducted as a slurry process using a liquid aprotic solvent or diluent, it is preferred to conduct the process at one or more temperatures in the range of about 200° C. to about 240° C. The reaction may be conducted at atmospheric, sub-atmospheric or super-atmospheric pressures. In many cases it is desirable as well as convenient to carry out the reaction in a closed system at autogenous pressures. Reaction periods will typically fall in the range of about 2 to about 48 hours, and preferably in the range of about 5 to about 20 hours. It will be appreciated that on the basis of this disclosure, departures from any of the ranges of proportions and/or reaction conditions given above may be made whenever such departures are deemed necessary or desirable.

The following Examples 1–12 illustrate the present halogen exchange process when performed without use of an ancillary solvent or diluent. These and all ensuing examples herein are for the purpose of illustration and not limitation.

EXAMPLES 1–12

A facility of the type schematically depicted in FIG. 1 is used. It comprises a 50-liter capacity stainless steel reactor (316S) 10 fitted with an electrical heating system (not depicted), bottom discharge valve 12, vapor condenser 14, receiver 16, vacuum system 18, a pressure release system (not depicted) that operates via the overheads, nitrogen line 20 for vacuum breaking, pressure gauge/monitor 22, temperature gauge/monitor 24, and manway 26 for solids charging. Reactor 10 is capable of operating at working pressures up to 125 psi, and vacuum system 18 has the capability of operating to 10 mmHg pressure. Agitator 28 is preferably a modified gate-type agitator having scraping knife-edges on the gate agitator to minimize sticking of the semi-molten paste-like reaction mass especially at the reactor wall. The facility should also include a spray drier (not depicted).

In the operation of the facility freshly prepared anhydrous potassium fluoride is used for each batch. This is conveniently prepared by forming a 40% weight/volume solution of potassium fluoride, heating the solution to the boiling point and pumping the solution via a dried atomizer into a drier operated at 350° to 400° C., e.g., 370° C. The dry powder is placed into suitable containers and used immediately. Alternatively, an activated form of KF such as referred to above, or a commercially available spray dried KF (whether milled or not milled), can be used. Before initiating a reaction, steps should be taken to ensure that the reactor 10 and the overheads are clean and dry, that all systems are operational, and that all raw materials are available for use. In addition the system should be checked to ensure that the bottom valve 12 is closed. If there is any doubt as regards vessel dryness, the reactor should be heated to 105° C. with full vacuum applied for two hours. After two hours the vessel should be allowed to cool while under vacuum. At ambient temperature the vacuum is then broken with nitrogen, and at this point the reaction procedure may be commenced.

At the start of the batch operation, reactor agitator 28 should be activated to be sure that the agitator is running smoothly. To the reactor with the agitator in operation, 21 kg of dry potassium fluoride powder is charged via manway 26. Then through the manway are charged 15 kg of hexachlorobenzene followed by 0.96 kg of tetrakis(diethylamino)-phosphonium bromide. Manway 26 and valve 30 are closed. The reactor contents are then heated over a period of one hour to 180° C. It is important to use this rapid heating to ensure sufficient agitation of this particular reaction mixture. During the heating the pressure in the reactor rises gradually. When the reactor contents reach 180° C., the reactor heating controls are adjusted to provide a heating rate increase of 4° C. per six hours. The reactor contents are allowed to heat up over this rate over 42 hours (7 increments of temperature increase for a total temperature increase of 28° C.). Slow heating at this stage of the process is important to ensure adequate mixing of this particular reaction mixture. At this point the reaction mixture should have reached a temperature of approximately 208° C. and the internal pressure of the reactor is monitored hourly. When the pressure does not vary between two successive hourly readings, the reaction can be deemed to have proceeded to completion. When the pressure becomes constant in the range of 75–100 psi the heating system is turned off and the reactor is allowed to cool. At this point valve 30 is cautiously opened to allow the pressure to vent from the reactor to condenser 14 and thence to receiver 16. When ambient pressure is reached in the reactor nitrogen is slowly introduced via nitrogen line 20. Vacuum system 18 is put into operation to provide a vacuum of about 725 mmHg to reactor 10. The nitrogen bleed to the reactor is slowly reduced while observing the rate of distillate recovery to receiver 16 to ensure that distillate recovery is not excessive. The vacuum is then gradually increased while continuing to monitor distillate recovery rate until maximum (flat) vacuum is achieved. When the system reaches ambient temperature the vacuum is broken with nitrogen, the vacuum system is shut off, and then the nitrogen bleed is discontinued. The reaction product mixture is then recovered from the reactor through valve 12. The reactor is cleaned with boiling aqueous caustic solution, washed with water and dried. A series of 12 batch operations was conducted generally in accordance with this procedure. The facility was as described except that in Examples 1 and 2, a low speed gate agitator was used. Because of tackiness of the reaction mixture, portions of the mixture tended to stick to the reactor wall. This problem was reduced by changing the agitator used in the remainder of the operations so that it included the above-referred-to knife-blades on the gate agitator. The conditions and results of these 12 runs are summarized in Table 1 along with the conditions and results of a control run where no catalyst was used. The acronyms in the Table are: HCB is hexachlorobenzene, CPFB is chloropentafluorobenzene, and DCTFB is dichlorotetrafluorobenzene.

TABLE 1

| Ex. No. | KF Charged, kg | HCB Charged, kg | Catalyst Charged, kg | Molar Ratio, KF:HCB | Reaction Time, hr | HFB Yield, kg | CPFB Yield, kg | DCTFB Yield, kg | Conversion of HCB, % | % Molar Yield HFB + CPFB |
|---|---|---|---|---|---|---|---|---|---|---|
| —* | 34.0 | 15.0 | None | 11.1:1 | 24 | 2.5 | 2.5 | — | — | 49 |
| 1 | 15.4 | 11.0 | 0.97 | 6.866:1 | 60 | 2.555 | 2.608 | 0.7353 | 77.64 | 69 |
| 2 | 15.4 | 11.0 | 0.98 | 6.866:1 | 82 | 2.4336 | 2.8137 | 0.6253 | 77.67 | 70 |
| 3 | 15.4 | 11.0 | 0.98 | 6.866:1 | 32 | 3.0964 | 2.9500 | 0.7906 | 90.21 | 81 |
| 4 | 21.0 | 15.0 | 1.30 | 6.867:1 | 22.5 | 3.7200 | 4.0000 | 1.2090 | 85.98 | 76 |
| 5 | 21.0 | 15.0 | 1.03 | 6.867:1 | 20 | 3.7011 | 4.2515 | 0.1900 | 78.95 | 78 |
| 6 | 21.0 | 15.0 | 1.03 | 6.867:1 | 46 | 4.5472 | 2.8490 | 1.8282 | 88.96 | 73 |
| 7 | 21.0 | 15.0 | 0.942 | 6.867:1 | 38 | 3.9763 | 4.1376 | 0.1900 | 81.09 | 79 |
| 8 | 21.0 | 15.0 | 0.96 | 6.867:1 | 44 | 3.9861 | 3.8378 | 0.7416 | 83.16 | 77 |
| 9 | 21.0 | 15.0 | 0.96 | 6.867:1 | 29.5 | 2.7824 | 4.1454 | 1.9082 | 83.86 | 67 |
| 10 | 21.0 | 15.0 | 0.96 | 6.867:1 | 34.5 | 3.1420 | 4.1447 | 1.7954 | 86.54 | 71 |
| 11 | 21.0 | 15.0 | 0.96 | 6.867:1 | 46 | 4.3521 | 4.1302 | 1.2931 | 94.41 | 83 |
| 12 | 21.0 | 15.0 | 0.96 | 6.867:1 | 46 | 4.4160 | 4.3008 | 1.1232 | 95.19 | 86 |

*Control run.

In the Table, reaction time is the time from reaching reaction temperature of 190° C. and yields of products are expressed as kilograms derived from analysis of the fraction of hexafluorobenzene, chloropentafluorobenzene and dichlorotetrafluorobenzene flash distilled from the respective reaction mixtures. Fractional distillation of the combined products from Examples 1–12 matched these analytical results almost exactly. Examples 1–12 yielded 104.765 kilograms of mixed chlorofluorobenzenes. The bulk fractional distillation resulted in the isolation and recovery of:

41.085 kg of Hexafluorobenzene 43.020 kg of Chloropentafluorobenzene 11.440 kg of Dichlorotetrafluorobenzene Each such product assayed 99% minimum purity.

It is to be noted that in the above examples, the catalyzed process of this invention was conducted at a maximum temperature of 208° C. without use of any added ancillary solvent or diluent. A conventional non-catalyzed non-solvent reaction of hexachloro-benzene with potassium fluoride typically involves use of 20-liter autoclaves operating at a temperature of 450° C. and a pressure of up to 1,500 psi and employs an 85% excess of potassium fluoride. Based on total raw material input, batch yield of desired products is around 12%.

A number of modifications in the process are possible without departing from the scope of this invention. By way of illustration and not limitation, the following modifications are presented:

a) The catalyst or catalyst residues may be recycled.

b) When the desired product is a polyfluoroaromatic compound, intermediates formed that contain a lesser than desired number of fluorine atoms per molecule may be recycled.

c) If the desired product has suitably high volatility, it may be removed from the reaction zone during the course of the reaction, e.g., essentially as soon as it is formed, so as to prevent or at least minimize-overfluorination.

d) Special procedures, e.g., drying by azeotropic distillation or by high temperature spray drying, may be employed for drying the alkali metal fluoride before use.

e) Multistage drying procedures may be used for drying the alkali metal fluoride before use.

f) The alkali metal fluoride may be micronized or reduced to a colloidal state in one or more stages prior to use.

g) Combinations of one or more drying stages with one or more micronizing stages, or vice versa, may be applied to the alkali metal fluoride before use.

h) Whether operating with or without an ancillary solvent, the alkali metal fluoride may be an optimized mixture composed of a major amount of dry, finely-divided potassium fluoride with a minor reaction-enhancing amount of dry, finely-divided cesium fluoride.

i) When producing a desired product having one or more intermediates that are in the liquid state at or below the selected reaction temperature(s), such intermediates may be employed as solvent/diluents in the process.

j) The proportions of the selected ingredients for use in any given situation may, and should be, optimized by performing carefully designed pilot experiments and scale-up trials before settling upon the mode of operation in a large scale commercial facility.

k) In lieu of or in addition to one or more simple alkali metal fluorides, e.g. KF, the alkali metal reactant may be or include a more complex alkali metal salt such as a double salt, examples of which include $KBF_4$, $CsBF_4$, $NaBF_4$, $K_3AlF_6$, $K_2SnF_6$, $Cs_2SnF_6$, $KPF_6$, $CsPF_6$, $K_2SiF_6$, $Cs_2SiF_6$, $Na_2TiF_6$, $K_2TiF_6$, $Na_2ZrF_6$, $K_2ZrF_6$, $Na_2HfF_6$, $K_2HfF_6$, among others.

l) In lieu of or in addition to one or more aminophosphonium catalysts of the type described herein, corresponding aminoarsonium compounds, $[(R_2N)_4As]X$, or aminoantimonium compounds, $[(R_2N)_4Sb]X$, where R and X are as defined above, may be used as catalyst or co-catalyst ingredients.

m) Simple quaternary phosphonium salts such as tetraethylphosphonium bromide, tetraphenylphosphonium bromide, tetraethylphosphonium chloride, tetraphenylphosphonium chloride, tetraethylphosphonium iodide, tetraphenylphosphonium iodide, etc., may be used as co-catalyst ingredients.

An example of one such modification which constitutes an embodiment of this invention relates to the synthesis of chloropentafluorobenzene and/or hexafluorobenzene from hexachlorobenzene. In this process the alkali metal fluoride ingredient used preferably comprises potassium fluoride, and the aminophosphonium catalyst ingredient used is preferably at least one tetra(dialkylamino)phosphonium halide (especially tetra(diethylamino)phosphonium bromide), and the agitated mixture formed from hexachlorobenzene, potassium fluoride, and the aminophosphonium catalyst ingredient is heated at one or more reaction temperatures in the range of 170° to 240° C. (preferably in the range of 200+ to 230° C.) for at least a substantial portion of the reaction. In this particular embodiment the agitated mixture comprises solids suspended or dispersed in continuous liquid phase, which preferably comprises a major amount (preferably 60 volume % or more at the outset of the reaction) of at least one chlorofluoroperhalobenzene that is in the liquid state at least while the agitated mixture is at one or more reaction temperatures in the range of 170° to 240° C. Examples of such chlorofluoroperhalobenzenes include dichlorotetrafluorobenzene (b.p. at atmospheric pressure, approximately 151° C.), trichlorotrifluorobenzene (m.p., approximately 62° C.), and tetrachlordifluorobenzene (m.p., approximately 138° C.). Of these, dichlorotetrafluorobenzene is particularly desirable as it is a liquid at room temperature and can readily be kept in the liquid state at temperatures in the range of 170° to 220° C. by conducting the reaction at suitable superatmospheric pressures.

It is preferred to conduct the halogen exchange reaction as a slurry process using at least one aprotic solvent or diluent. When conducting the halogen exchange process as a slurry process, the reaction mixture should be anhydrous or substantially anhydrous before reaching the temperature at which the halogen exchange reaction is initiated, and preferably the reaction mixture should be anhydrous or substantially anhydrous ab initio. The term "substantially anhydrous" as used in this document with reference to the reaction mixture, i.e., the mixture of the reactants, catalyst(s), and solvent(s), means that the total water content of the mixture at the commencement of the exchange reaction at about 160° C. or above is below about 2000 ppm (wt/wt) and preferably below about 1500 ppm. In general, the lower the water content, the better. Excessive water can kill the reaction. Therefore it is desirable not only to use anhydrous or substantially anhydrous alkali metal fluoride (not more than about 3000 ppm, as noted above), but to ensure that the other components being used are sufficiently dry (i.e., have water contents, if any, that are sufficiently low as to keep the total water content of the overall mixture below about 2000 ppm (wt/wt) and preferably below about 1500 ppm. For example, if industrial grades of polar aprotic solvents contain excessive amounts of water, it is desirable to dry the solvent to a level of, say, 100 ppm, preferably down to a level of about 50 ppm (wt/wt) by means of azeotropic distillation or use of molecular sieves. It is usually very difficult to produce, maintain and use chemicals, especially in a large scale chemical facility, in an absolutely anhydrous condition. Thus the term "anhydrous" is used herein in the same sense as those skilled in the art understand the term. Thus, if by chance the substance used has absolutely zero water content, it is, of course "anhydrous". But even if it does not have zero water content, as long as the water content is in the trace range so that the effect of the water present is of no material consequence and the water content complies with manufacturer's specifications and/or designations of "anhydrous", the substance is deemed herein to be "anhydrous". Without limiting the generality of the foregoing, one commercial supplier, Aldrich Chemical Company, in its 1996–1997 Catalog Handbook of Fine Chemicals refers to a group of listed "anhydrous solvents" on page 1773 thereof as having a water content of <0.005%. Other suppliers may specify other maximum water contents for their "anhydrous" grades, so there is no exact fine line of distinction between "anhydrous" and "substantially anhydrous".

The following Examples 13–21 illustrate procedures for conducting the halogen exchange process as a slurry process in an aprotic solvent. All parts given in these examples are by weight.

EXAMPLE 13

The reaction equipment used is a reactor equipped with heating means, mechanical stirrer, charge and discharge ports, and an overhead take-off line for feeding vaporous product from the reactor to an intermediate portion of a fractionation column. The column in turn is equipped with an overhead line for collecting the chloropentafluorobenzene and a line for returning the condensed bottoms from the condenser to a discharge point in the reactor below the liquid level therein. A mixture of 285 parts of hexachlorobenzene, 406 parts of anhydrous ball-milled potassium fluoride powder, 600 parts of sulfolane, and 80 parts of tetrakis (diethylamino)phosphonium bromide is heated with stirring at 200° C. for 40 hours while continuously removing and fractionating the volatiles. The overhead from the column is chloropentafluorobenzene. The bottoms from the column are continuously returned to below the surface of the slurry within the reactor.

EXAMPLE 14

A mixture of 285 parts of hexachlorobenzene, 406 parts of anhydrous potassium fluoride powder activated by the procedure of T. P. Smyth, A. Carey and B. K. Hodnett (loc. cit.), 80 parts of tetrakis(diethylamino)phosphonium bromide, 600 parts of triglyme, and 80 parts of potassium fluoborate is heated in the above reactor with stirring at 195° to 210° C. for 40 hours. Vaporous perchlorofluorobenzenes are continuously taken off overhead and fractionated as in Example 1.

EXAMPLE 15

The procedure of Example 13 is repeated in the same manner except that 80 parts of 18-crown-6 ether is also included in the initial reaction mixture.

EXAMPLE 16

The procedure of Example 13 is repeated in the same manner except that 80 parts of 25 crypt 222 is also included in the initial reaction mixture.

EXAMPLE 17

The procedure of Example 14 is repeated in the same manner except that 80 parts of 18-crown-6 ether is also included in the initial reaction mixture.

EXAMPLE 18

The procedure of Example 13 is repeated in the same manner except that 150 parts of a mixture of pentachlorofluorobenzene, tetrachlorodifluorobenzene, and trichlorotrifluorobenzene (such as recovered from the reaction mixture of a prior reaction) is also included in the initial reaction mixture, and a total of 450 parts of spray dried potassium fluoride is charged to the reactor.

EXAMPLE 19

The procedure of Example 13 is repeated in the same manner except that 80 parts of 18-crown-6 ether and 150 parts of dichlorotetrafluorobenzene, are also included in the initial reaction mixture, and a total of 450 parts of spray dried potassium fluoride is charged to the reactor.

Example 20 which follows, illustrates a preferred process for pretreating the quaternary phosphonium catalyst to remove therefrom at least a portion, inter alia, quaternary ammonium halide impurity. Further details concerning such process are set forth in commonly-owned co-pending application Ser. No. 08/975,924 filed Nov. 21, 1997, and incorporated herein by reference. In Examples 21 and 22 the pretreated, purified catalyst was used, and in Example 23 the original non-pretreated catalyst was used. A comparison between Examples 22 and 23 performed in the same way illustrates the advantages of using a pretreated, purified catalyst when practicing any of the embodiments of this invention.

EXAMPLE 20

To a 1-liter flask containing 156 grams of tetrahydrofuran was added with stirring 38.90 grams of tetrakis (diethylamino)phosphonium bromide catalyst (Chordip Limited, England, 75% purity). The residual insoluble material (2.8 grams) was filtered from the solution, and was determined by $^1$H-NMR to be primarily tetraethylammonium bromide. To the tetrahydrofuran solution of the catalyst was then added 245 grams of anhydrous diethyl ether resulting in the precipitation of the tetrakis(diethylamino) phosphonium bromide catalyst. The solid catalyst was then filtered and dried under full vacuum at about 50° C. for one hour. The purified catalyst (29.8 grams) was analyzed by $^{31}$P-NMR and was found to be at least 95% pure.

EXAMPLE 21

To a 1-liter stainless steel stirred pressure reactor was added a solution of 12 grams of purified catalyst from Example 20 in 421 grams of benzonitrile (Aldrich, <50 ppm water), 164 grams of spray-dried potassium fluoride (Hashimoto Chemical Corporation, Japan, 0.87 $m^2$/g), and 115 grams of hexachlorobenzene. The overhead of the reactor comprised of a ½ inch-OD column packed with 15-inch long Pro-Pak® packing, an air-cooled partial condenser (also known as a knockback condenser), an air-cooled total condenser, and a product receiver with a back-pressure control valve. The reaction mixture, a slurry, was heated and maintained at 218° to 220° C. for 5 hours while maintaining the system pressure at 14 psig and the column distillate temperature at 140° C. The vaporized perhalobenzenes, predominately chloropentafluorobenzene and some hexafluorobenzene, were carried to the overhead about as soon as they were formed, and thereupon were condensed and recovered. Concurrently, other condensed perhalobenzenes were being returned from the knockback condenser to the reaction mixture. At the end of the 5-hour reaction period, the heating was discontinued and all the volatile products remaining in the reactor were removed by distillation by application of progressively increased vacuum to the system in order to recover all volatile products formed in the reaction. The entire distillate product mixture was analyzed by gas chromatography. The yields, based on hexachlorobenzene, and were 2.5% hexafluorobenzene, 58.6% chloropentafluorobenzene, 23.8% dichlorotetrafluorobenzene, and 7.5% trichlorotrifluoro-benzene.

EXAMPLE 22

A solution of 12.0 grams of purified tetrakis (diethylamino)phosphonium chloride catalyst from Example 20 in 420 grams of benzonitrile (Aldrich, <50 ppm water) was charged to a 1-liter stainless steel stirred pressure reactor. Spray-dried potassium fluoride (164 grams, Hashimoto Chemical Corporation, Japan, 0.87 $m^2$/g) and hexachlorobenzene (115 grams) were then added to the reactor. The reaction mixture was reacted for 5.5 hours at 220° C. The heating was then discontinued and all the volatile products were removed by simple distillation at progressively increased vacuum. The distillate mixture was analyzed by gas chromatography. The yields, based on hexachlorobenzene, were 24.4% hexafluorobenzene, 39.9% chloropentafluorobenzene, 21.9% dichlorotetrafluorobenzene, and 8.1% trichlorotrifluorobenzene.

EXAMPLE 23

A solution of 15.1 grams of tetrakis(diethylamino) phosphonium chloride (Chordip Limited; 75% purity) in 420 grams of benzonitrile (Aldrich, <50 ppm water) was charged to a 1-liter stainless steel stirred pressure reactor. Spray-dried potassium fluoride (164 grams, Hashimoto Chemical Corporation, Japan, 0.87 $m^2/g$) and hexachlorobenzene (115 grams) were then added to the reactor. The reaction mixture was reacted for 6.5 hours at 220° C. The heating was then discontinued and all the volatile products were removed by simple distillation at progressively increased vacuum. The distillate mixture was analyzed by gas chromatography. The yields, based on hexachlorobenzene, were 34.7% hexafluoro-benzene, 37.7% chloropentafluorobenzene, 12.3% dichlorotetrafluorobenzene, and 3.9% trichlorotrifluorobenzene.

A most efficacious way presently known for carrying out the halogen exchange process in order to produce perhalobenzenes having at least 3, preferably at least 4, and more preferably either 5 or 6 fluorine atoms on the ring is a process which comprises heating a slurry formed from ingredients comprising (i) at least one finely-divided alkali metal fluoride having an atomic number of 19 or more, (ii) a perhalobenzene of the formula $C_6F_nX_{6-n}$ where n is 0 to 4, and each X is, independently, a chlorine or bromine atom, (iii) a tetra(dihydrocarbylamino)phosphonium halide catalyst, most preferably tetrakis(diethyl-amino) phosphonium bromide or chloride, and (iv) at least one halogen-free, polar, aprotic solvent, preferably benzonitrile and/or an alkyl-substituted benzonitrile that is in the liquid state at a temperature at least as low as 20° C., and/or nitrobenzene under conditions to form perhalobenzene having at least 3, preferably at least 4, and most preferably 5 or 6 fluorine atoms per molecule. The most efficacious way of producing perhalobenzenes having either 5 and/or 6 fluorine atoms on the ring is the process which comprises:

a) heating the above slurry formed from the foregoing ingredients comprising (i)–(iv) at one or more reaction temperatures at which a vapor phase comprising at least one perhalobenzene having at least 5 fluorine atoms per molecule is formed; and b) continuously removing vapor phase from the slurry;

c) separating perhalobenzene having at least 5 fluorine atoms on the ring from the vapor phase; and d) returning all or at least a portion of the remainder of the component(s) of the vapor phase, if any, into the slurry.

In a preferred embodiment, steps c) and d) are conducted continuously so that steady state conditions exist in the reaction zone. It is also preferred that the initial water content of the slurry is below about 1500 ppm on a weight basis before heating to the selected reaction temperature(s). Also the slurry preferably is formed from about 5 to about 8 moles of said alkali metal fluoride and from about 0.05 to about 0.3 mole of said catalyst per mole of perhalobenzene used in forming the slurry. When this process is used for producing chloropentafluorobenzene as the main product, a preferred starting material is hexachloro-benzene, and the reaction conditions in the reaction zone are maintained such that when the reaction slurry is at the selected reaction temperature(s) (most preferably no higher than about 250° C.), the amount, if any, of chloropentafluorobenzene in the liquid phase of the slurry averages no more than about 5 percent by weight based on the total weight of the liquids in the slurry. In such cases the vapor phase is typically composed of vaporized polar, aprotic solvent, hexafluorobenzene, chloropentafluorobenzene, dichlorotetrafluorobenzene, and trichlorotrifluorobenzene, and most preferably, of the perhalobenzenes in the vapor phase, chloropentafluorobenzene is present in the largest amount.

II. PREPARATION OF POLYMERIZATION CATALYSTS AND THEIR PRECURSORS

The discovery of the unprecedented effectiveness aminophosphonium catalysts in a halogen exchange reaction makes it possible pursuant to this invention to produce industrially important end products with greater efficiency and reduced costs as compared to most, if not all, prior halogen exchange technology. Some of the improvements in, and applications of, this discovery are described below.

Production of Pentafluorophenylorganometallic Compounds

Production of pentafluorophenylorganometallic compounds is effected by a process which comprises (A) producing a perhalobenzene having 5 fluorine atoms on the ring, preferably chloropentafluorobenzene, by a halogen exchange reaction catalyzed by use of an aminophosphonium catalyst, preferably a tetra(dihydrocarbylamino) phosphonium halide catalyst, and most preferably tetrakis (diethylamino)phosphonium bromide or chloride; and (B) reacting perhalobenzene produced and recovered in the process of (A) with a Grignard reagent under conditions forming a pentafluorophenyl Grignard reagent, preferably by a Grignard exchange reaction. These steps (A) and (B) can be performed in one continuous sequential operation in a given plant facility, or these steps can be conducted separately at different times, and also at different plant locations.

Alternatively, in step (B), perhalobenzene produced and recovered in the process of (A) can be reacted under carefully controlled conditions (e.g., very low temperatures such as 78° C. with an alkali metal alkyl of the formula MR, where M is an alkali metal such as lithium, sodium or potassium, and R is an alkyl group having 4 to about 12 carbon atoms under conditions forming pentafluorophenyl alkali metal compound such as $C_6F_5Li$, $C_6F_5Na$, or $C_6F_5K$. Because these alkali metal compounds can be explosive, this alternative process, while feasible, is not recommended.

In conducting the Grignard exchange reaction it is preferred to react chloropenta-fluorobenzene with a $C_3$ to $C_{20}$ hydrocarbyl magnesium halide Grignard reagent in an ether solvent and under anhydrous reaction conditions. Preferred $C_3$ to $C_{20}$ hydrocarbyl magnesium halide Grignard reagents are those in which the halide is bromide or iodide and in which the hydrocarbyl group is an alkyl, alkenyl, cycloalkyl, cycloalkenyl, aryl or aralkyl group, and Grignard reagents having 2 to 10 carbon atoms are the more preferred reactants. Most preferred are the isopropyl magnesium halides, especially the bromide. While proportions can be varied, it is best to employ about 1–2 moles of chloropentafluorobenzene per mole of the hydrocarbyl Grignard reagent used as the reactant. For further details concerning this preferred halogen exchange procedure, see Krzystowczyk et al., EP 728,760 A2, published Aug. 28, 1996.

Example 24, which is based in part on the halogen exchange process of the foregoing published EP application of Krzystowczyk et al., illustrates a preferred procedure for conducting this process.

EXAMPLE 24

In a drybox, 31.45 g of chloropentafluorobenzene prepared as in Example 21 above (0.155 mole) and 64.42 g of a 2 molar ether solution of isopropylmagnesium bromide (iPrMgBr) (0.141 mole) are charged to a Fisher Porter reactor and heated to 60° C. for 4.5 hours. Pentafluorophenylmagnesium bromide is formed.

When using bromopentafluorobenzene in the Grignard exchange reaction, ethyl magnesium bromide can be used as the initial Grignard reagent. However as shown by Tamborski, et al., *J. Organometal. Chem.*, 1971, 26, 153–156, it is desirable to use short reaction periods when employing that procedure.

Production of pentafluorophenyl alkali metal compounds pursuant to this invention is best accomplished by reacting perhalobenzene produced and recovered in the halogen exchange process such as in Example 21 above with an alkali metal alkyl such as butyllithium or ethylsodium at −78° C. in an anhydrous paraffinic or cycloparaffinic hydrocarbon medium (e.g., hexane or heptane) under an inert atmosphere. Alternatively, controlled reaction of metallic sodium with chloropentafluorobenzene or bromopentafluorobenzene in an inert hydrocarbon or ether reaction medium at −78° C. can be used to produce the alkali metal pentafluorophenyl alkali metal compound. In this case any solids formed are removed by filtration or other similar procedure. Normally small portions of the alkali metal are introduced slowly into a hydrocarbon or ether solution of the chloropentafluorbenzene or bromopentafluorbenzene while stirring the resulting reaction mixture and maintaining the mixture at a temperature at about −78° C.

Production of Pentafluorophenyl Boron Compounds

To produce pentafluorophenyl boron compounds, the process comprises the following steps conducted sequentially, either in one continuous operation or in a series of two or three separate operations which can be conducted at different time periods at a given plant site, or at different plant locations:

A) producing a perhalobenzene having 5 fluorine atoms on the ring, preferably chloropentafluorobenzene, by a halogen exchange process catalyzed by use of an aminophosphonium catalyst, preferably a tetra (dihydrocarbylamino)phosphonium halide catalyst, and most preferably tetrakis(diethylamino) phosphonium bromide or chloride;

B) converting perhalobenzene from A) into a pentafluorophenyl organometallic compound, preferably a pentafluorphenyl Grignard reagent, using a process such as described above, and C) converting pentafluorophenyl organometallic compound from B) into a pentafluorophenyl boron compound by reacting the pentafluorophenyl organometallic compound with a boron trihalide or an etherate complex thereof, preferably boron trifluoride or a boron trifluoride etherate complex.

In performing this process, it is preferred to form chloropentafluorobenzene in A), form pentafluoromagnesium bromide Grignard reagent in ethyl ether in B), and form tris(pentafluorophenyl)boron (also known as tris (pentafluorophenyl)borane) in C) by reacting the Grignard reagent with boron trifluoride etherate in ethyl ether.

Example 25, based in part on the above Krzystowczyk et al. published EP application, illustrates the synthesis of tris(pentafluorophenyl)borane from pentafluorophenylmagnesium bromide.

EXAMPLE 25

To a four-neck round bottom flask is added 131 mmoles of the pentafluorophenyl-magnesium bromide solution in diethyl ether formed as in Example 24 above. To this solution is charged 5.84 g (41.4 mmoles) of boron trifluoride diethyletherate while maintaining the temperature at 0° C. The resulting solution is allowed to warm to room temperature and is stirred for 16 hours whereby tris (pentafluorophenyl)borane is formed.

Production of Tetra(pentafluorophenyl)boron Anion

In order to produce tetra(pentafluorophenyl)boron anion, the process comprises the following steps conducted sequentially, either in one continuous or intermittent operation at a given plant site, or in a series of two or more separate operations which can be conducted at different time periods and at different plant sites:

A) producing a perhalobenzene having 5 fluorine atoms on the ring, preferably chloropentafluorobenzene, by a halogen exchange process catalyzed by use of an aminophosphonium catalyst, preferably a tetra (dihydrocarbylamino)phosphonium halide catalyst, and most preferably tetrakis(diethylamino) phosphonium bromide or chloride;

B) converting perhalobenzene from A) into a pentafluorophenyl organometallic compound using a process such as described above, C) converting pentafluorophenyl organometallic compound from B) into a pentafluorophenyl boron compound by reacting the organometallic compound with a boron trihalide or an etherate complex thereof, preferably boron trifluoride or a boron trifluoride etherate complex such as described above, and D) converting pentafluorophenyl boron compound from C) in a suitable solvent or diluent into a single coordination complex that comprises a labile tetra (pentafluoro-phenyl)boron anion.

In conducting this operation it is preferred in C) to mix together in an ether medium, a pentafluorophenyl Grignard reagent and boron trifluoride or a boron trifluoride etherate in proportions of about 4.1 to about 4.5 moles of the Grignard reagent per mole of the BF$_3$, and maintain the temperature in the range of about 25 to about 45° C. The product of this reaction is an ether-soluble complex, $(C_6F_5)_4BMgX$. Likewise, it is preferred in D) to mix together an aqueous solution of a hydrocarbyl ammonium chloride or bromide such as N,N-dimethylanilinium chloride or tributylammonium chloride, and the ethereal solution of the complex formed in C) by slowly adding the aqueous hydrocarbyl ammonium halide solution to the ether solution of the complex formed in C) while keeping the temperature at about 5° C. or below and stirring the mixture. In this reaction use of an excess of the hydrocarbyl ammonium chloride or bromide is desirable.

Examples 26 and 27 illustrate production of N,N-dimethylanilinium tetrakis(penta-fluorophenyl)borane and tributylammonium tetrakis(pentafluorophenyl)borane, respectively, which are typical coordination complexes that comprise a labile tetra(pentafluorophenyl)boron anion and a cation capable of irreversibly reacting with a ligand (e.g., a methyl group) bonded to the transition metal atom of a Group 4 metallocene to thereby form an ionic catalyst composition.

EXAMPLE 26

Boron trifluoride diethyl etherate (138.7 g, 0.98 mole) is added to a diethyl ether solution of pentafluorophenylmagnesium bromide (3326 g, 4.17 moles) formed as in Example 24. The addition is at a rate allowing the mixture to reach reflux temperature. The mixture is heated at reflux for 18 hours. This mixture is then cooled to −10° C. and N,N-dimethylanilinium chloride (1142 grams, 2.06 moles) previously formed from concentrated HCl, water, and N,N-dimethylaniline is slowly added while keeping the temperature at about 0° C. After the addition, the mixture is stirred for one hour at −5° C. to 0° C. Then the two phases are separated, and the organic phase is washed with water and dried over MgSO$_4$. The N,N-dimethylanilinium tetrakis (pentafluorophenyl)borane is precipitated by addition of hexane with stirring, and recovered by filtration.

EXAMPLE 27

Tributylammonium tetrakis(pentafluorophenyl)borane is produced by substituting 2.06 moles of tributylammonium chloride for the N,N-dimethylanilinium chloride.

Production of Active Polymerization Catalysts

To produce one type of active polymerization catalysts suitable for use in forming homopolymers and copolymers of polymerizable monoolefin, diolefin, and acetylenic monomers, the process comprises the following steps conducted sequentially, either in one continuous operation or in a series of two or more separate operations which can be conducted at different time periods either at one plant site or at two or more different plant sites:

A) producing a perhalobenzene having 5 fluorine atoms on the ring, preferably chloropentafluorobenzene, by a halogen exchange process catalyzed by use of an aminophosphonium catalyst, preferably a tetra (dihydrocarbylamino)phosphonium halide catalyst, and most preferably tetrakis(diethylamino) phosphonium bromide or chloride;

B) converting perhalobenzene from A) into a pentafluorophenyl organometallic compound using a process such as described above, C) converting pentafluorophenyl organometallic compound from B) into a pentafluorophenyl boron compound by reacting the organometallic compound with a boron trihalide or an etherate complex thereof, preferably boron trifluoride or a boron trifluoride etherate complex such as described above, D) converting pentafluorophenyl boron compound from C) in a suitable solvent or diluent into a single coordination complex that comprises a labile tetra (pentafluoro-phenyl)boron anion such as described above, and E) forming an active catalyst by a process comprising mixing together in a suitable solvent or diluent, (i) a cyclopentadienyl metal compound containing a Group 4 transition metal, and (ii) at least a second component comprising said complex, under conditions and for a period of time such that the cation of said complex reacts irreversibly with at least one ligand of the cyclopentadienyl compound, and such that the pentafluorophenyl anion forms a non-coordinating ion pair with a resulting cation produced from the cyclopentadienyl metal compound.

The following examples further illustrate the preparation of active catalysts and use of such catalysts in the polymerization of unsaturated monomers to form useful polymeric materials. Examples 28–50 are based in part on Examples appearing in U.S. Pat. No. 5,198,401, and Examples 51–56 are based in part on U.S. Pat. No. 5,153,157.

EXAMPLE 28

To a one-liter stainless-steel autoclave containing a dry nitrogen atmosphere are charged 400 mL of dry, oxygen-free hexane, a solution of 15 mg of bis(cyclopentadienyl)-hafnium dimethyl in 30 mL of toluene, and then a toluene solution (50 mL) containing 12 mg of bis(cyclopentadienyl) hafnium dimethyl and 30 mg of tri(n-butyl)ammonium tetrakis(pentafluorophenyl)boron formed as in Example 27 above. The autoclave is pressured with 90 psig of ethylene and stirred at 60° C. for one hour. The autoclave is vented and opened and the polyethylene formed is recovered.

EXAMPLE 29

To the autoclave of Example 15 previously purged with dry nitrogen are charged 400 mL of dry, oxygen-free hexane, and a solution of 9 mg of bis(tert-butylcyclopenta-dienyl) zirconium dimethyl and 2.9 mg of N,N-dimethylanilinium tetrakis(pentafluoro-phenyl)boron formed as in Example 26 above, in 25 mL of toluene. The autoclave is then charged with 100 mL of 1-butene and further pressured with 65 psig of ethylene and stirred at 50° C. for one hour. The autoclave is vented, cooled and the contents dried. The ethylene-1-butene copolymer formed in the process is recovered.

EXAMPLE 30

To a one-liter stainless-steel autoclave containing a dry nitrogen atmosphere are charged 400 mL of dry, oxygen-free hexane, a solution of 15 mg of bis(cyclopentadienyl)-hafnium dimethyl in 25 mL of toluene, and then a toluene solution (50 mL) containing 17 mg of bis(cyclopentadienyl) hafnium dimethyl and 42 mg of tri(n-butyl)ammonium tetrakis(pentafluorophenyl)boron formed as in Example 27 above. Propylene (200 mL) was added and the autoclave is pressured with 50 psig of ethylene and stirred at 60° C. for fifteen minutes. The autoclave is vented and opened and the residual hexane in the contents evaporated under a stream of air. The ethylene and propylene formed are recovered.

EXAMPLES 31–38

Using procedures as in Examples 28–30 a series of catalyst compositions are prepared and polymerization runs are performed, all pursuant to this invention. Table 1 summarizes the materials used in the respective polymerization runs. In each run summarized in Table 2, the anion source is either tributylammonium tetrakis(pentafluoro-phenyl)boron (BAPFB) produced as in Example 27 above or N,N-dimethylanilinium tetrakis(pentafluorophenyl)boron (MAPFB) produced as in Example 26 above. The Group 4 metallocene and the anion source are added in each case as a solution in an appropriate amount of toluene.

TABLE 2

| Ex. | Group 4 compound (mg) | Anion Source (mg) | Ancillary Diluent | Temp. | Time | Monomer(s) |
|---|---|---|---|---|---|---|
| 31 | (Cp)$_2$Hf(Me)$_2$ (36) | MAPFB (11) | None* | 50° C. | 15 min. | Propylene (400 mL), ethylene (120 psig) |
| 32 | (Cp)$_2$Hf(Me)$_2$ (12) | BAPFB (30) | Hexane | 50° C. | 60 min. | 1-Butene (50 mL), ethylene (65 psig) |

TABLE 2-continued

| Ex. | Group 4 compound (mg) | Anion Source (mg) | Ancillary Diluent | Temp. | Time | Monomer(s) |
|---|---|---|---|---|---|---|
| 33 | (Cp)$_2$Hf(Me)$_2$ (19) | BAPFB (15) | Hexane | 50° C. | 45 min. | 1-Butene (50 mL), propylene (25 mL), ethylene (60 psig) |
| 34 | (Cp)$_2$Hf(Me)$_2$ (72) | MAPFB (16) | Hexane | 50° C. | 10 min. | 1,4-Hexadiene (100 mL), propylene (50 mL), ethylene (90 psig) |
| 35 | (Cp)$_2$Hf(Me)$_2$ (27) | BAPFB (30) | Hexane | 50° C. | 60 nun. | 1-Hexene (100 mL), ethylene (65 psig) |
| 36 | (Cp)$_2$Hf(Me)$_2$ (72) | MAPFB (22) | Hexane | 40° C. | 65 min. | Propylene (200 mL) |
| 37 | (Cp)$_2$Hf(Me)$_2$ (77) | MAPFB (22) | None* | 40° C. | 90 min. | Propylene (400 mL) |
| 38 | rac-dimethylsilyl(In)$_2$Hf(Me)$_2$ (10) | MAPFB (5) | None* | 40° C. | 270 min. | Propylene (500 mL) |

*Polymerization conducted in bulk propylene.

EXAMPLE 39

To a polymerization vessel are added 0.22 g of tributylammonium tetrakis(pentafluorophenyl)boron (produced as in Example 27 above) in 50 mL of toluene, followed by 0.1 g of bis(pentamethylcyclopentadienyl)zirconium dimethyl. The vessel is capped with a rubber septum and stirred at room temperature for 10 minutes. Then the vessel is pressured with 1.5 atmospheres of ethylene and stirred vigorously. After 15 minutes the reaction vessel is vented and methanol is added to destroy the catalyst. Linear polyethylene is recovered from the resulting mixture.

EXAMPLE 40

The procedure of Example 39 is repeated with the following changes: 0.34 g of the anion source produced as in Example 27 above is used, the Group 4 metallocene used is 0.13 g of (cyclopentadienyl)(pentamethylcyclopentadienyl) zirconium dimethyl, and the reaction is terminated with methanol after 10 minutes. Polyethylene is produced.

EXAMPLE 41

Polyethylene is produced by conducting the procedure of Example 39 with the following changes: 0.18 g of the same anion source produced as in Example 27 above is used, the Group 4 metallocene is 0.12 g of bis[1,3-bis(trimethylsilyl) cyclopentadienyl]-zirconium dimethyl, and the reaction is terminated with methanol after 10 minutes.

EXAMPLE 42

The procedure of Example 39 is repeated except that 0.34 g of the anion source formed as in Example 27 above is used together with 0.1 g of bis(cyclopentadienyl)-zirconium dimethyl, and the polymerization reaction is terminated after 10 minutes. Polyethylene produced in the polymerization is recovered.

EXAMPLE 43

To a polymerization vessel are added 0.12 g of tributylammonium tetrakis(penta-fluorophenyl)boron (produced as in Example 27 above) and 0.04 g of bis(cyclopentadienyl)-zirconium dimethyl in 100 mL of toluene. The vessel is capped with a rubber septum and stirred at 60° C. for 3 minutes. Then 3 mL of 1-hexene and ethylene at 1.5 atmospheres are added to the vessel. After 20 minutes the reaction vessel is vented and methanol is added to deactivate the catalyst. An ethylene-hexene copolymer is recovered from the resulting mixture.

EXAMPLE 44

An active catalyst is formed pursuant to this invention by reacting 550 mg of bis(trimethylsilylcyclopentadienyl) hafnium dimethyl with 800 mg of N,N-dimethylanilinium tetrakis(pentafluorophenyl)boron (formed as in Example 26 above) in 50 mL of toluene in a polymerization vessel. On passing ethylene into the solution, an exothermic reaction occurs with the formation of polyethylene.

EXAMPLES 45–50

Six active catalysts are produced in accordance with this invention by mixing together in toluene the following components:

Ex. 45: 40 mg of N.N-dimethylanilinium tetrakis (pentafluorophenyl)boron (formed as in Example 26 above) and 17 mg of 1-bis(cyclopentadienyl)zircona-3-dimethylsilacyclobutane.

Ex. 46: 80 mg of N.N-dimethylanilinium tetrakis (pentafluorophenyl)boron (formed as in Example 26 above) and 36 mg of 1-bis(cyclopentadienyl)titana-3-dimethylsilacyclobutadiene.

Ex. 47: 85 mg of tributylammonium tetrakis (pentafluorophenyl)boron (formed as in Example 27 above) and 34 mg of bis(cyclopentadienyl)zirconium (2,3-dimethyl-1,3-butadiene.

Ex. 48: 39 mg of N.N-dimethylanilinium tetrakis (pentafluorophenyl)boron (formed as in Example 26 above) and 20 mg of 1-bis(cyclopentadienyl)hafna-3-dimethylsilacyclobutane.

Ex. 49: 41 mg of tributylammonium tetrakis (pentafluorophenyl)boron (formed as in Example 27 above) and 21 mg of bis(cyclopentadienyl)hafnium (2,3-dimethyl- 1,3-butadiene.

Ex. 50: 75 mg of N.N-dimethylanilinium tetrakis (pentafluorophenyl)boron (formed as in Example 26 above) and 53 mg of (pentamethylcyclopentadienyl)-(tetramethylcyclopentadienylmethylene)hafnium benzyl.

Polyethylene is produced by passing ethylene through each of these 6 respective catalyst solutions.

EXAMPLE 51

To an autoclave containing a dry nitrogen atmosphere are added a toluene solution (20 mL) containing 0.2 mmoles of triethylborane, and then a solution formed from 5 mL of toluene, 3 mg of bis(cyclopentadienyl)zirconium dimethyl, and 1.5 mg of N,N-dimethyl-anilinium tetrakis (pentafluorophenyl)boron produced as in Example 26 above. The vessel is pressured with 90 psig of ethylene and stirred at 40° C. for one hour. The vessel is vented and opened, and linear polyethylene is recovered from the autoclave.

EXAMPLE 52

Example 51 is repeated except that a toluene solution formed from 5 mL of toluene, 4 mg of bis(cyclopentadienyl) hafnium dimethyl and 1.5 mg of N,N-dimethylanilinium tetrakis(pentafluorophenyl)boron produced as in Example 26 above is used. Linear polyethylene is produced.

EXAMPLE 53

Example 51 is repeated except that a solution formed from 20 mL of toluene and 0.2 mmole of triethylaluminum is charged to the autoclave followed by a solution formed from 10 mL of toluene, 3 mg of bis(cyclopentadienyl) zirconium dimethyl and 3 mg of N,N-dimethylanilinium tetrakis(pentafluorophenyl)boron produced as in Example 26 above. Linear polyethylene is produced.

EXAMPLE 54

Example 51 is repeated except that after charging the toluene solution of triethylaluminum, a solution formed from 20 mL of toluene, 3 mg of bis(cyclopentadienyl)-hafnium dimethyl and 6 mg of N,N-dimethylanilinium tetrakis(pentafluorophenyl)boron produced as in Example 26 above is used. Linear polyethylene is produced.

EXAMPLE 55

To a one-liter stainless steel autoclave containing a dry nitrogen atmosphere are added 0.2 ml of a 35 wt % solution of triethylaluminum in hexane followed by 10 mL of a solution formed from 10 mL of toluene, 36 mg of bis(cyclopentadienyl)hafnium dimethyl, and 11 mg of N,N-dimethylanilinium tetrakis(pentafluorophenyl)boron produced as in Example 26 above. Propylene (400 mL) is added to the autoclave and the contents are heated to 40° C. The vessel is then pressured with 200 psig of ethylene and stirred at 40° C. for 0.5 hour. The vessel is vented and opened, and a copolymer of ethylene and propylene is recovered from the autoclave.

EXAMPLE 56

Example 43 is repeated except that the triethylaluminum is replaced by 0.2 mmole of triethylborane, and the ensuing solution used is formed from 10 mL of toluene, 24 mg of bis(cyclopentadienyl)hafnium dimethyl, and 8 mg of N,N-dimethylanilinium tetrakis(penta-fluorophenyl)boron produced as in Example 26 above. Produced is an ethylene-propylene copolymer.

EXAMPLES 57–71

Supported catalyst compositions are produced and used as polymerization catalysts by carrying out the procedures described in detail in the 15 examples of PCT published application WO 91/09882 A1 (as published Jul. 11, 1991), but in each case using N,N-dimethylanilinium tetrakis (pentafluorophenyl)boron formed as in Example 26 above. In each instance the unit cost of the catalyst is significantly reduced without sacrifice of operating efficiency.

Another process for producing supported catalysts comprises reacting a pentafluorophenyl boron compound produced pursuant to this invention such as described above, preferably so-produced tris(pentafluorophenyl)borane, with hydroxy groups of a metal/metalloid oxide support under conditions to form a support-bound anionic activator, and then contacting said support-bound anionic activator with a suitable metallocene of a Group 4 transition metal such that the activator protonates the metallocene whereby a supported ionic catalyst system is produced comprising a transition metal cation and a support bound anion. The supports should have surface hydroxyl groups exhibiting a $pK_a$ equal to or less than that of amorphous silica, i.e., a $pK_a$ less than or equal to about 11. Silica and silica-alumina meeting these criteria are preferred support materials. For complete details concerning procedures and materials suitable for use in preparing supported catalysts of this type one should refer to PCT Published Patent Application WO 96/04319 A1 as published on Feb. 15, 1996. Examples 72–92 illustrate this process.

EXAMPLES 72–92

Supported catalyst compositions are produced and used as polymerization catalysts by carrying out the procedures described in detail in Examples 1–21 of PCT published application WO 96/04319 A1 (as published Feb. 15, 1996), but in each case where tris(pentafluorophenyl)boron is used in forming the catalyst, the tris(pentafluorophenyl)boron used is produced as in Example 25 above. In each instance the unit cost of the catalyst is significantly reduced without sacrifice of operating efficiency.

Another group of active catalysts which can be produced with high efficiency and lower cost by use of this invention are catalysts formed by a process which comprises the following steps conducted sequentially, either in one continuous or discontinuous operation at a given plant site, or in a series of two or more separate operations which can be conducted at different time periods and at different plant sites:

A) producing a perhalobenzene having 5 fluorine atoms on the ring, preferably chloropentafluorobenzene, by a halogen exchange process catalyzed by use of an aminophosphonium catalyst, preferably a tetra(dihydrocarbylamino)phosphonium halide catalyst, and most preferably tetrakis(diethylamino) phosphonium bromide or chloride, B) converting perhalobenzene from A) into a pentafluorophenyl organometallic compound using a process such as described above, C) converting pentafluorophenyl organometallic compound from B) into a pentafluorophenyl boron compound by reacting the organometallic compound with a boron trihalide or an etherate complex thereof, preferably boron trifluoride or a boron trifluoride etherate complex such as described above, D) contacting pentafluorophenyl boron compound from C) with a metallocene of the formula $LMX_2$ wherein L is a derivative of a delocalized pi-bonded group imparting a constrained geometry to the metal active site and contains up to 50 non-hydrogen atoms, M is a Group 4 metal, and each X is, independently, hydride, or a hydrocarbyl, silyl, or germyl group having up to 20 carbon, silicon, or germanium atoms under conditions to form a catalyst having a limiting charge separated structure of the formula

wherein A is an anion formed from said pentafluorophenyl boron compound.

Of the pentafluorophenyl boron compounds suitable for use in this process, tris(pentafluorophenyl)borane is the most preferred reactant. Examples of suitable metallocenes of the formula $LMX_2$, as well as complete details for producing and using such catalysts, are set forth in EP 520,732 A1 as published Dec. 30, 1992, and in U.S. Pat. No. 5,132,380, issued to J. C. Stevens, et al. on Jul. 21, 1992.

Examples 93–207 further illustrate the production of active catalysts of the formula LMX⊕ XA⊖ and the utilization of such catalysts in the polymerization of unsaturated monomers to form useful polymeric materials.

EXAMPLES 93–207

Catalyst compositions are produced and used as polymerization catalysts by carrying out the procedures described in detail in the first 115 examples of EP 520,732 A1 (as published Dec. 30, 1992), but in each case where tris(pentafluorophenyl)boron is used, it is tris(pentafluorophenyl)boron produced as in Example 25 above. In each instance the unit cost of the catalyst is significantly reduced without sacrifice of operating efficiency.

It is to be understood that the ingredients referred to by chemical name or formula anywhere in the specification or claims hereof, whether referred to in the singular or plural, are identified as they exist prior to coming into contact with another substance referred to by chemical name or chemical type (e.g., another reactant, a solvent, a diluent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and other materials are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance or ingredient as it existed at the time just before it was first contacted, blended or mixed with one or more other substances or ingredients in accordance with the present disclosure. The fact that the substance or ingredient may have lost its original identity through a chemical reaction or transformation or complex formation or assumption of some other chemical form during the course of such contacting, blending or mixing operations, is thus wholly immaterial for an accurate understanding and appreciation of this disclosure and the claims thereof. Nor does reference to an ingredient by chemical name or formula exclude the possibility that during the desired reaction itself an ingredient becomes transformed to one or more transitory intermediates that actually enter into or otherwise participate in the reaction. In short, no representation is made or is to be inferred that the named ingredients must participate in the reaction while in their original chemical composition, structure or form.

Each and every patent or other publication or published document referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises (A) heating a mixture formed from ingredients comprising (i) at least one finely-divided alkali metal fluoride having an atomic number of 19 or more, (ii) at least one perhalobenzene of the formula $C_6F_nX_{6-n}$ where n is 0 to 4, and each X is, independently, a chlorine or bromine atom, and (iii) an aminophosphonium catalyst, at one or more reaction temperatures at which chloropentafluorobenzene or bromopentafluorobenzene is formed; (B) recovering chloropentafluorobenzene or bromopentafluorobenzene formed in (A); (C) converting chloropentafluorobenzene or bromopentafluorobenzene from (B) into a pentafluorophenyl Grignard reagent or a pentafluorophenyl alkali metal compound; and (D) converting pentafluorophenyl Grignard reagent or pentafluorophenyl alkali metal compound from (C) into a pentafluorophenyl boron compound by reacting the pentafluorophenyl Grignard reagent or pentafluorophenyl alkali metal compound with a boron trihalide or an etherate complex thereof.

2. A process according to claim 1 wherein the aminophosphonium catalyst ingredient comprises at least one tetra(dihydrocarbylamino)phosphonium halide.

3. A process according to claim 1 wherein the aminophosphonium catalyst ingredient is tetrakis(diethylamino)phosphonium bromide or tetrakis(diethylamino)phosphonium chloride.

4. A process according to claim 1 further comprising (E) converting pentafluorophenyl boron compound from (D) in a suitable solvent or diluent into a single coordination complex comprising a labile tetra(pentafluorophenyl)boron anion.

5. A process according to claim 4 wherein the aminophosphonium catalyst ingredient comprises at least one tetra(dihydrocarbylamino)phosphonium halide.

6. A process according to claim 4 wherein the aminophosphonium catalyst ingredient is tetrakis(diethylamino)phosphonium bromide or tetrakis(diethylamino)phosphonium chloride.

7. A process according to claim 1 further comprising (E) contacting said pentafluorophenyl boron compound from (D) with a metallocene of the formula $LMX_2$ wherein L is a derivative of a delocalized pi-bonded group imparting a constrained geometry to the metal active site and contains up to 50 non-hydrogen atoms, M is a Group 4 metal, and each X is, independently, hydride, or a hydrocarbyl, silyl, or germyl group having up to 20 carbon, silicon, or germanium atoms under conditions to form a catalyst having a limiting charge separated structure of the formula LMX⊕ XA⊖ wherein A is an anion formed from said pentafluorophenyl boron compound.

8. A process according to claim 7 wherein the aminophosphonium catalyst ingredient comprises at least one tetra(dihydrocarbylamino)phosphonium halide.

9. A process according to claim 7 wherein the aminophosphonium catalyst ingredient is tetrakis(diethylamino)phosphonium bromide or tetrakis(diethylamino)phosphonium chloride.

10. A process which comprises (A) heating a mixture formed from ingredients comprising (i) at least one finely-divided alkali metal fluoride having an atomic number of 19 or more, (ii) at least one perhalobenzene of the formula $C_6F_nX_{6-n}$ where n is 0 to 4, and each X is, independently, a chlorine or bromine atom, and (iii) an aminophosphonium catalyst, at one or more reaction temperatures at which chloropentafluorobenzene or bromopentafluorobenzene is formed; (B) recovering chloropentafluorobenzene or bromopentafluorobenzene formed in (A); (C) converting chloropentafluorobenzene or bromopentafluorobenzene from (B) into a pentafluorophenyl Grignard reagent; and (D) converting pentafluorophenyl Grignard reagent from (C) into a tris(pentafluorophenyl)borane by reacting the pentafluorophenyl Grignard reagent with a boron trihalide or an etherate complex thereof.

11. A process according to claim 10 wherein the aminophosphonium catalyst ingredient is one or more tetra(dialkylamino)phosphonium chlorides or bromides in which the alkyl groups can be the same or different and each has up to about 12 carbon atoms.

12. A process according to claim 10 wherein the aminophosphonium catalyst ingredient is tetrakis(diethylamino) phosphonium bromide.

13. A process according to claim 10 further comprising (E) converting tris(pentafluorophenyl)borane from (D) in a suitable solvent or diluent into a single coordination complex comprising a labile tetra(pentafluorophenyl)boron anion.

14. A process according to claim 13 wherein the aminophosphonium catalyst ingredient is one or more tetra(dialkyl amino)phosphonium chlorides or bromides in which the alkyl groups can be the same or different and each has up to about 12 carbon atoms.

15. A process according to claim 13 wherein the aminophosphonium catalyst ingredient is tetrakis(diethylamino) phosphonium bromide.

16. A process according to claim 10 further comprising (E) contacting tris(pentafluorophenyl)borane from (D) with a metallocene of the formula $LMX_2$ wherein L is a derivative of a delocalized pi-bonded group imparting a constrained geometry to the metal active site and contains up to 50 non-hydrogen atoms, M is a Group 4 metal, and each X is, independently, hydride, or a hydrocarbyl, silyl, or germyl group having up to 20 carbon, silicon, or germanium atoms under conditions to form a catalyst having a limiting charge separated structure of the formula $LMX \oplus XA \ominus$ wherein A is an anion formed from said pentafluorophenyl boron compound.

17. A process according to claim 16 wherein the aminophosphonium catalyst ingredient is one or more tetra (dialkylamino)phosphonium chlorides or bromides in which the alkyl groups can be the same or different and each has up to about 12 carbon atoms.

18. A process according to claim 16 wherein the aminophosphonium catalyst ingredient is tetrakis(diethylamino) phosphonium bromide.

19. A process according to any of claims 1, 4, 7, 10, 13 or 16 wherein ingredient (i) as used in forming said mixture is principally or exclusively finely-divided anhydrous or substantially anhydrous potassium fluoride having an average surface area of at least about 40 m²/g.

20. A process according to any of claims 3, 6, 9, 12, 15, or 18 wherein ingredient (i) as used in forming said mixture is finely-divided, anhydrous or substantially anhydrous spray-dried potassium fluoride having a water content of 1000 ppm or below and an average surface area of at least about 85 m²/g.

21. A process according to any of claims 1, 4, 7, 10, 13, or 16 wherein said mixture, at least when heated to at least one of said one or more reaction temperatures, is predominately a mixture of solids dispersed in a continuous liquid phase comprising at least one halogen-free, polar, anhydrous or substantially anhydrous aprotic solvent.

22. A process according to any of claims 3, 6, 9, 12, 15, or 18 wherein (A) is conducted in (i) nitrobenzene, (ii) at least one liquid alkylmononitrobenzene, or (iii) a mixture of (i) and (ii).

23. A process which comprises:
A) heating a slurry formed from ingredients comprising (i) at least one finely-divided alkali metal fluoride having an atomic number of 19 or more, (ii) a perhalobenzene of the formula $C_6F_nX_{6-n}$ where n is 0 to 4, and each X is, independently, a chlorine or bromine atom, (iii) a tetra(dihydrocarbylamino)phosphonium halide catalyst, and (iv) at least one halogen-free, polar, aprotic solvent at one or more reaction temperatures at which a vapor phase comprising perhalobenzene having at least 5 fluorine atoms on the ring, is formed;
B) continuously removing vapor phase from the slurry;
C) separating and recovering chloropentafluorobenzene or bromopentafluorobenzene from the vapor phase;
D) returning all or at least a portion of the remainder of the component(s) of the vapor phase, if any, into the slurry;
E) converting chloropentafluorobenzene or bromopentafluorobenzene separated and recovered in C) into a pentafluorophenyl Grignard reagent or a pentafluorophenyl alkali metal compound; and
F) converting said pentafluorophenyl Grignard reagent or pentafluorophenyl alkali metal compound into a pentafluorophenyl boron compound by reacting the pentafluorophenyl Grignard reagent or pentafluorophenyl alkali metal compound with a boron trihalide or an etherate complex thereof.

24. A process which comprises:
A) heating a slurry formed from ingredients comprising (i) at least one finely-divided alkali metal fluoride having an atomic number of 19 or more, (ii) a perhalobenzene of the formula $C_6F_nX_{6-n}$ where n is 0 to 4, and each X is, independently, a chlorine or bromine atom, (iii) a tetra(dihydrocarbylamino)phosphonium halide catalyst, and (iv) at least one halogen-free, polar, aprotic solvent at one or more reaction temperatures at which a vapor phase comprising perhalobenzene having at least 5 fluorine atoms on the ring, is formed;
B) continuously removing vapor phase from the slurry;
C) separating and recovering chloropentafluorobenzene or bromopentafluorobenzene from the vapor phase;
D) returning all or at least a portion of the remainder of the component(s) of the vapor phase, if any, into the slurry; and
E) converting chloropentafluorobenzene or bromopentafluorobenzene separated and recovered in C) into a pentafluorophenyl Grignard reagent by a Grignard exchange reaction performed in an ether reaction medium.
F) converting said pentafluorophenyl Grignard reagent into tris(pentafluorophenyl)borane by reacting in an ether reaction medium, the pentafluorophenyl Grignard reagent with boron trifluoride or an etherate complex thereof.

25. A process according to claim 23 further comprising:
G) converting at least a portion of said pentafluorophenyl boron compound in a suitable solvent or diluent into a single coordination complex that comprises a labile tetra(pentafluorophenyl)boron anion.

26. A process according to claim 24 further comprising:
G) converting at least a portion of said tris (pentafluorophenyl)borane in a suitable solvent or diluent into a single coordination complex comprising a labile tetra(pentafluorophenyl)boron anion.

27. A process according to claim 26 wherein said complex is a hydrocarbylammonium tetra(pentafluorophenyl)boron complex that is soluble in said solvent or diluent.

28. A process according to claim 26 wherein said complex is a trialkylammonium tetra(pentafluorophenyl)boron complex or an N,N-dimethylanilinium tetra(pentafluoro-phenyl)boron complex.

29. A process according to any of claims 25–28 further comprising:

H) forming an active catalyst by a process comprising mixing together in a suitable solvent or diluent, (A) a cyclopentadienyl metal compound containing a Group 4 transition metal, and (B) at least a second component comprising said complex, under conditions and for a period of time such that the cation of said complex reacts irreversibly with at least one ligand of the cyclopentadienyl compound, and such that the pentafluorophenyl anion forms a non-coordinating ion pair with a resulting cation produced from the cyclopentadienyl metal compound.

30. A process according to claim 29 wherein the mixture formed in H) further comprises at least one additional component which is (C) at least one organometallic additive compound of the formula $R_3M$ wherein each R is, independently, a hydrocarbyl group or an alkoxide group with the proviso that at least one R is a hydrocarbyl group, and wherein M is an aluminum or boron atom; or (D) a catalyst support; or (E) a combination of (C) and (D).

31. A process according to claim 30 wherein said additional component is at least one trihydrocarbylaluminum compound or at least one trihydrocarbylboron compound.

32. A process according to claim 30 wherein said additional component is an inorganic oxide in particulate form.

33. A process according to claim 32 wherein said inorganic oxide is silica, alumina or silica-alumina.

34. A process according to claim 23 further comprising:

G) reacting at least a portion of said pentafluorophenyl boron compound with hydroxy groups of a metal oxide support under conditions to form a support-bound anionic activator, and then contacting said support-bound anionic activator with a suitable metallocene of a Group 4 transition metal such that the activator protonates the metallocene whereby a supported ionic catalyst system is produced comprising a transition metal cation and a support bound anion.

35. A process according to claim 24 further comprising:

G) reacting at least a portion of said tris(pentafluorophenyl)borane with hydroxy groups of a silica or silica-alumina support under conditions to form a support-bound anionic activator, and then contacting said support-bound anionic activator with a suitable metallocene of a Group 4 transition metal such that the activator protonates the metallocene whereby a supported ionic catalyst system is produced comprising a transition metal cation and a support bound anion.

36. A process according to claim 23 further comprising:

G) contacting said pentafluorophenyl boron compound with a metallocene of the formula $LMX_2$ wherein L is a derivative of a delocalized pi-bonded group imparting a constrained geometry to the metal active site and contains up to 50 non-hydrogen atoms, M is a Group 4 metal, and each X is, independently, hydride, or a hydrocarbyl, silyl, or germyl group having up to 20 carbon, silicon, or germanium atoms under conditions to form a catalyst having a limiting charge separated structure of the formula $LMX \oplus XA \ominus$ wherein A is an anion formed from said pentafluorophenyl boron compound.

37. A process according to claim 24 further comprising:

G) contacting said tris(pentafluorophenyl)borane with a metallocene of the formula $LMX_2$ wherein L is a derivative of a delocalized pi-bonded group imparting a constrained geometry to the metal active site and where L contains up to 50 non-hydrogen atoms, M is a Group 4 metal, and each X is, independently, hydride, or a hydrocarbyl, silyl, or germyl group having up to 20 carbon, silicon, or germanium atoms under conditions to form a catalyst having a limiting charge separated structure of the formula $LMX \oplus XA \ominus$ wherein A is an anion formed from the tris(pentafluorophenyl)borane.

* * * * *